(12) United States Patent
Pyun et al.

(10) Patent No.: US 12,030,895 B2
(45) Date of Patent: Jul. 9, 2024

(54) METHOD FOR PREPARING HETEROCYCLIC DERIVATIVE COMPOUND, COMPOSITION CONTAINING SAME COMPOUND, AND HYDRATE OF SAME COMPOUND

(71) Applicant: JW PHARMACEUTICAL CORPORATION, Seoul (KR)

(72) Inventors: Do Kyu Pyun, Gyeonggi-do (KR); Kyoung Jin Oo, Gyeonggi-do (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 0 days.

(21) Appl. No.: 18/386,093

(22) Filed: Nov. 1, 2023

(65) Prior Publication Data
US 2024/0083911 A1   Mar. 14, 2024

Related U.S. Application Data

(62) Division of application No. 17/859,566, filed on Jul. 7, 2022, now Pat. No. 11,866,448, which is a division of application No. 16/615,566, filed as application No. PCT/KR2018/005932 on May 24, 2018, now abandoned.

(30) Foreign Application Priority Data

May 25, 2017   (KR) ..................... 10-2017-0064914

(51) Int. Cl.
   *C07D 498/04*   (2006.01)
   *A61K 9/20*   (2006.01)
   *C07C 63/06*   (2006.01)
   *C07C 63/10*   (2006.01)

(52) U.S. Cl.
   CPC ............. *C07D 498/04* (2013.01); *A61K 9/20* (2013.01); *C07C 63/06* (2013.01); *C07C 63/10* (2013.01); *C07B 2200/13* (2013.01)

(58) Field of Classification Search
   CPC ........ C07D 498/04; C07C 63/06; C07C 63/10
   See application file for complete search history.

(56) References Cited

U.S. PATENT DOCUMENTS

| | | |
|---|---|---|
| 2007/0010670 A1 | 1/2007 | Hirata et al. |
| 2008/0064871 A1 | 3/2008 | Hirata et al. |
| 2008/0305169 A1 | 12/2008 | Miki et al. |
| 2011/0028467 A1 | 2/2011 | Ahn et al. |

FOREIGN PATENT DOCUMENTS

| | | |
|---|---|---|
| JP | H11-515033 A | 12/1999 |
| JP | 4646068 B2 | 3/2011 |
| KR | 10-2011-0005688 A | 1/2011 |
| WO | WO-1997-17363 A1 | 5/1997 |
| WO | WO-2008-062740 A1 | 5/2008 |
| WO | WO-2009/145456 A2 | 12/2009 |

OTHER PUBLICATIONS

Chemical Abstract Compound, STN Express, RN 1955558-27-6, (Entered STN: Jul. 19, 2016).
Cho, H., et al. (2014) "Synthesis of a Human Urate Transporter-1 Inhibitor, an Arginine Vasopressin Antagonist, and a 17β-Hydroxysteroid Dehydrogenase Type-3 Inhibitor, Using Ring-Expansion of Cyclic Ketoximes with DIBALH.", Chem. Pharm. Bull. 62(4):354-363.
International Search Report dated Sep. 7, 2018 issued in International Patent Application No. PCT/KR2018/005932, with English translation.
Campion, E. W., et al.; "Asymptomatoc Hyperuricemia—Risks and Consequences in the Normative Aging Study", The American Journal of Medicine, vol. 82, Mar. 1987, pp. 421-426.
McGinnity, D. F., et al.; "Prediction of CYP2C9-Mediated Drug-Drug Interactions: a Comparison Using Data From Recombinant Enzymes and Human Hepatocytes", Drug Metabolism and Disposition, vol. 33, No. 11, Jun. 1, 2005, pp. 1700-1707.
Hautekeete, M. L., et al.; "Severe hepatotoxicity related to benzarone: a report of three cases with two fatalities" Liver, 2005, 15, pp. 25-29.
Arai, M., et al.; "Letter to the Editor—Fulminant Hepatic Failure Associated With Benzbromarone Treatment: a Case Report", Journal of Gastroenterology and Hepatology (2002) 17, 625-626.
Kaufmann, P., et al.; "Mechanisms of Benzarone and Benzbromarone-Induced Hepatic Toxicity", Hepatology, vol. 41, No. 4, Apr. 2005, pp. 925-935.
Kunishima, C., et al.; "Benzbromarone (Urinorm®) の代謝・毒性および薬理作 用に関する研究", J Saitama Med School 2003;30:187-194.
Vervaeck, M., et al.; "Sudden hypotonic paraparesis caused by tophaceous gout of the lumbar spine", Clin Neurol Neurosur 1991, vol. 93-103, pp. 233-236.
Office Action (Non-Final) from corresponding U.S. Appl. No. 16/615,566, dated May 18, 2021.
Office Action (Final) from corresponding U.S. Appl. No. 16/615,566, dated Nov. 26, 2021.

(Continued)

*Primary Examiner* — Rebecca L Anderson
(74) *Attorney, Agent, or Firm* — Harness, Dickey & Pierce, P.L.C.

(57) ABSTRACT

The present invention relates to: a novel method for preparing a heterocyclic derivative compound of chemical formula I below; a novel intermediate compound used in the preparation method; a composition for treatment or prevention of hyperuricacidemia, gout, nephritis, chronic renal insufficiency, nephrolith, uremia, urolithiasis, or a uric acid-related disease, the composition containing the compound of chemical formula I at a dose of more than 2 mg and equal to or less than 10 mg and being orally administered once a day; and a hydrochloride 1.5 hydrate of the novel compound of chemical formula I.

2 Claims, 13 Drawing Sheets

(56) References Cited

OTHER PUBLICATIONS

Office Action (Non-Final) from corresponding U.S. Appl. No. 16/615,566, dated May 2, 2022.
Advisory Action from corresponding U.S. Appl. No. 16/615,566, dated Jan. 24, 2022.
Sung Oh Ahn et al., J Pharmacol Exp Ther 357: 157-166, Apr. 2016.
De Souza et al.; Journal of the American Association of Laboratory Animal Science, vol. 57, No. 1, Jan. 2018, pp. 13*17.
Office Action from corresponding U.S. Appl. No. 17/859,603, dated Jan. 4, 2023.
Nair AB, Jacob S. A simple practice guide for dose conversion between animals and human. J Basic Cln Pharma 2016; 7:27-31.
USFDA. Guidance for Industry: Estimating the Maximum Safe Starting Dose in Adult Healthy Volunteer. Rockville, MD: US Food and Drug Administration; 2005.
Final Office Action from Corresponding U.S. Appl. No. 17/859,603, Dated Jul. 12, 2023.
Notice of Allowance from corresponding U.S. Appl. No. 17/859,566, dated Aug. 21, 2023.

METHOD FOR PREPARING HETEROCYCLIC DERIVATIVE COMPOUND, COMPOSITION CONTAINING SAME COMPOUND, AND HYDRATE OF SAME COMPOUND

CROSS-REFERENCE TO RELATED APPLICATIONS

This application is a divisional application of U.S. patent application Ser. No. 17/859,566, filed on 7 Jul. 2022, which is a divisional application of U.S. patent application Ser. No. 16/615,566, filed on Nov. 21, 2019, which is a national phase application of PCT Application No. PCT/KR2018/005932, filed on May 24, 2018, which claims the benefit and priority to Korean Patent Application No. 10-2017-0064914, filed on May 25, 2017. The entire disclosures of the applications identified in this paragraph are incorporated herein by references.

FIELD

The present invention relates to a new process for preparing a heterocycle derivative compound of the following Formula I; a new intermediate compound used in the above process; a composition for the treatment or prevention of hyperuricemia, gout disease, nephritis, chronic renal failure, nephrolithiasis, uremia, urolithiasis, or a disease associated with uric acid, which comprises the compound of Formula I at a dose of greater than 2 mg to 10 mg or less and is orally administered once daily; and a new hydrochloride 1.5 hydrate (sesquihydrate) of the compound of Formula I:

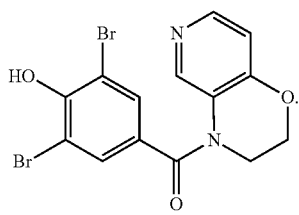

I

BACKGROUND

Currently used agents for the treatment or prophylaxis of hyperuricemia and gout include Benzbromarone which is a uricosuric agent having an inhibitory activity of human urate anion transporter 1 (hURAT1), as well as Probenecid and Sulfinpyrazone. However, these drugs do not have sufficient activities on URAT1. In particular, Benzbromarone has some demerits in the aspect of adverse effects. Benzbromarone shows a strong inhibitory function to 2C9 protein among cytochrome P450 (CYP450) proteins and thus has a possibility of drug-drug interaction. Formation of reactive metabolites also has been reported from glutathione (GSH) conjugate formation experiments [Dermot F. McGinnity et al., Drug Metabolism and Disposition, 33, p 1700-1707 (2005)].

Furthermore, since Benzbromarone has a benzofuran backbone similar to the drug structures of Benziodarone, Benzarone and Amiodarone which are drugs reported to show hepatotoxicity, it has a problem of incidence of death cases due to hepatotoxicity induction as well as adverse effect of liver injury. Therefore, the liver function of patients who intend to take this drug must be examined before the administration, and even during the administration it is recommended in therapy to check out for a certain period (six months) on whether hepatotoxicity has been induced or not. Hence, a drug that solves these problems is required in the medical field [Hautekeete M. L., et al., Liver, 15, p 25-29 (1995); Makoto Arai, et al., Journal of Gastroenterology and Hepatology 17, p 625-626 (2002); Saitama Medical College Magazine, 30, p 187-194 (2003); Priska Kaufmann, et al., HEPATOLOGY, 41, p 925-935 (2005)].

PCT Publication No. WO 2009/145456 (C&C Research Laboratories) discloses heterocycle derivative compounds of the following [Formula I], among the specific examples of which is (3,5-dibromo-4-hydroxyphenyl)-(2,3-dihydro-4H-pyrido[4,3-b][1,4]oxazin-4-yl)-methanone (Compound 4):

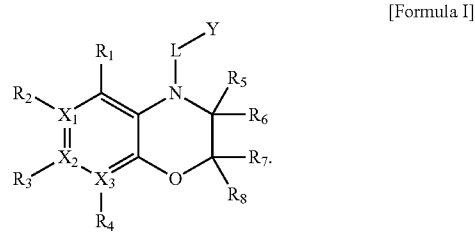

[Formula I]

PCT Publication No. WO 2009/145456 discloses that the above heterocycle derivative compounds show a strong inhibitory activity on human urate anion transporter 1 (hURAT1) as compared with conventional inhibitors of hURAT1 activity and thus are useful as an inhibitor, specifically a selective inhibitor, of uric acid reuptake. It also discloses that the compounds show no drug-drug interaction on cytochrome P450 (CYP450), show a selectivity between organic anion transporters, have higher solubility and metabolic stability so as to show advantageous pharmacokinetics, and thus show an excellent effect compared with conventional drugs in the treatment or prophylaxis of hyperuricemia, acute gouty arthritis, chronic gouty arthritis, tophus (gouty node), gout nephrosis, nephritis, chronic renal failure, nephrolithiasis, uremia, urolithiasis and complications reported to be accompanied with uric acid increase in blood such as hyperlipidemia, ischemic heart disease, myocardial infarction, arteriosclerosis, cerebral infarction, cerebrovascular disease, diabetes and hypertension.

The above document describes an experiment in which the above heterocycle derivative compounds were orally administered to Cebus monkeys at 3.75 mg/kg, 7.5 mg/kg, and 15 mg/kg. When these doses are theoretically converted to a dose value that is applicable to humans, they amount to about 15 mg to 60 mg, and at such high doses the risk of side effects is substantial.

Further, in the case of the hydrochloride salt of the above heterocycle derivative compounds, due to its hygroscopic property there was a limitation in formulating its preparation for oral administration by a wet granulation method.

In addition, as a method for synthesizing the heterocycle derivative compounds, the above document also discloses a process for preparing the heterocycle derivative compounds of Formula I, comprising the steps of: (1) halogenating a compound of the following Formula VII to obtain a compound of the following Formula X and then reacting the obtained compound of Formula X with a compound of the following Formula IX to obtain a compound of the following Formula VIII, or alternatively carrying out a Mitsunobu reaction of the compound of Formula VII and the compound of Formula IX to obtain the compound of Formula VIII; (2) cyclizing the obtained compound of Formula VIII to obtain a compound of the following Formula IV; and (3) carrying out a peptide coupling reaction of the obtained compound of Formula IV with a compound of the following Formula III:

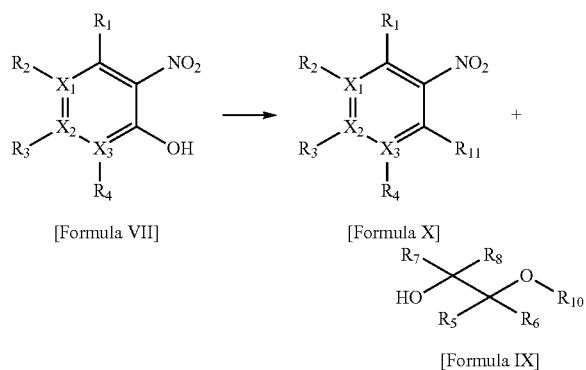

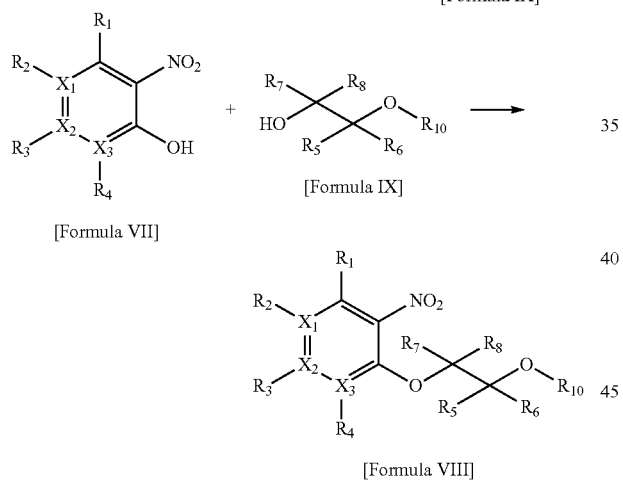

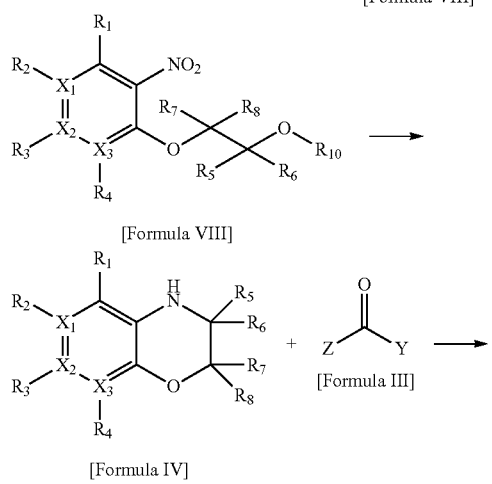

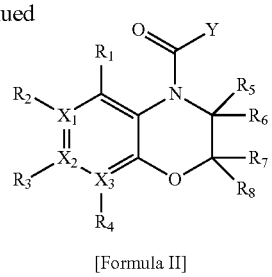

[Formula II]

However, among the oxazine derivatives of the above [Formula IV] obtained as an intermediate in the above preparation method, 3,4-dihydro-2H-pyrido[4,3-b][1,4] oxazine derivative having the following structure is liquid and unstable, and its degradation causes a problem of generating impurities that are likely to cause carcinogenicity or mutagenesis. Since an additional process for purifying these impurities is required, the above preparation method is not suitable for large-scale production.

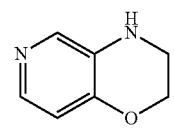

Furthermore, 3,5-dibromo-4-methoxy-benzoyl chloride having the following structure, which is the compound of the above [Formula III] in the above-mentioned preparation method, is obtained from the expensive starting material, 3,5-dibromo-4-methoxybenzoic acid. In addition, the process of synthesizing the compound of the [Formula III] with the oxazine derivative of the [Formula IV] has a possibility of generating a genetic mutation, and thus a process capable of minimizing such a possibility is required.

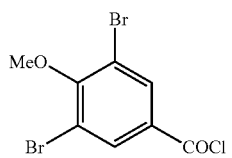 [SMILES: COc1c(Br)cc(C(=O)Cl)cc1Br]

US Patent Publication No. US 2007-0010670 A1 (Japan Tobacco Inc.) discloses an oxazine derivative compound of the following formula effective for the treatment of hyperuricemia, gout and the like, and a method of synthesizing the same:

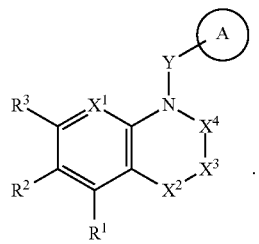

SUMMARY

Problem to be Solved

The previous method for preparing the heterocycle derivative compounds of Formula I has a problem in that the degradation of the oxazine derivative obtained as an intermediate generates impurities that are likely to cause carcinogenicity or mutagenesis, and another problem in that the synthesis reaction of the above oxazine derivative with 3,5-dibromo-4-methoxy-benzoyl chloride generates toxic intermediates that induce a genetic mutation. It also has a disadvantage in that additional purification steps are required to remove impurities at each step, and thus the preparation method must go through a number of steps, thereby it is not suitable for large-scale production. In order to resolve these problems, it is intended by the present invention to provide a new process for preparing the heterocycle derivative compound of Formula I, characterized by employing a novel oxazine derivative HBr salt (dihydrobromide, 2HBr), which is a stabilized form of the above oxazine derivative, and a novel benzoic acid intermediate that does not generate a toxic-inducing substance and is capable of in situ reaction, thereby reducing the preparation steps and thus is suitable for large-scale production.

Furthermore, the present invention is intended to provide novel intermediate compounds used in the above preparation method.

Furthermore, the present invention is intended to provide a composition for use in the treatment or prevention of hyperuricemia, gout disease, nephritis, chronic renal failure, nephrolithiasis, uremia, urolithiasis, or a disease associated with uric acid, which comprises as an active ingredient the compound of Formula I, or a pharmaceutically acceptable salt thereof or a hydrate thereof at a dose of greater than 2 mg to 10 mg or less based on the free base of the compound of Formula I and is orally administered once daily.

Furthermore, the present invention is intended to provide a novel hydrochloride 1.5 hydrate (sesquihydrate) of the compound of Formula I.

Technical Solution to the Problem

The present invention provides a process for preparing a compound of the following Formula I, or a pharmaceutically acceptable salt thereof or a hydrate thereof, comprising coupling-reacting a compound of the following Formula III with a compound of the following Formula IV:

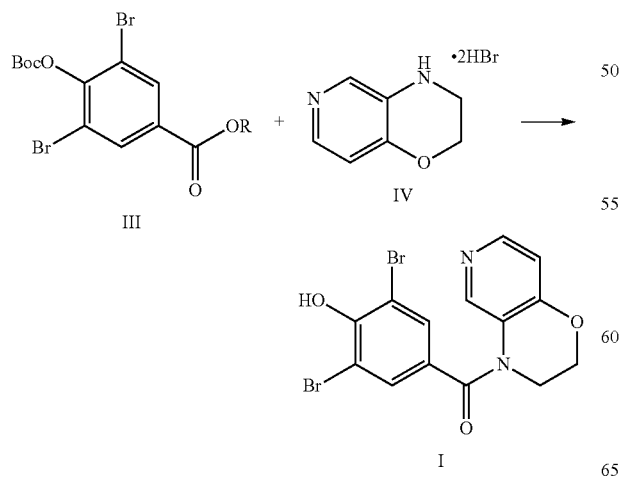

wherein R is hydrogen or tert-butyloxycarbonyl (Boc).

In one embodiment of the present invention, the compound of Formula III can be obtained by reacting a compound of the following Formula II with di-tert-butyl dicarbonate and pyridine.

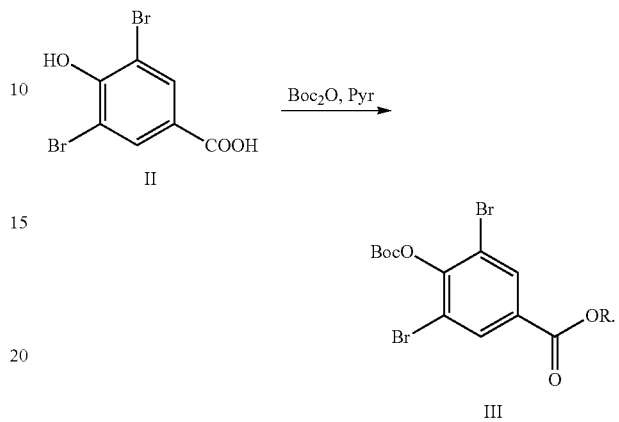

In one embodiment of the present invention, the above process for preparing the compound of Formula I may comprise the following steps: (1) reacting the compound of Formula III with the compound of Formula IV to obtain a compound of Formula V; (2) reacting the compound of Formula V with an alcohol in the presence of an acid to obtain a salt of the compound of Formula I; and (3) reacting the salt of the compound of Formula I with a base first and then with an acid secondarily:

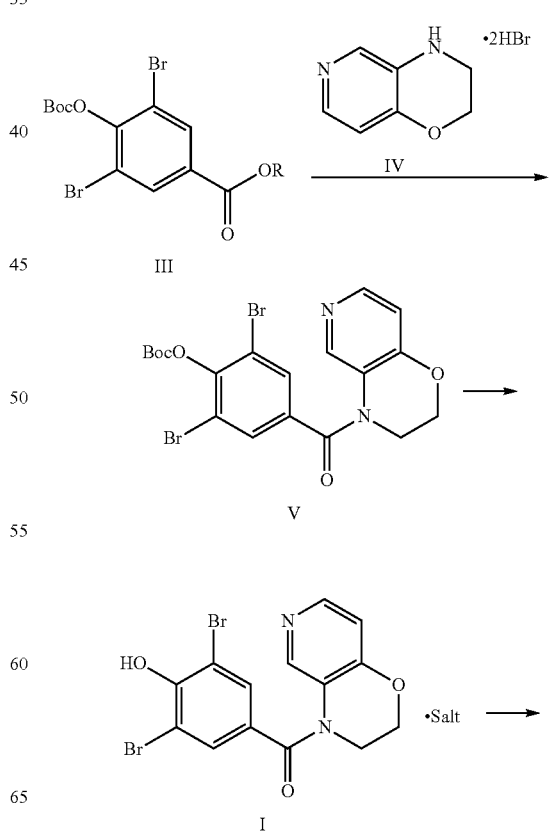

-continued

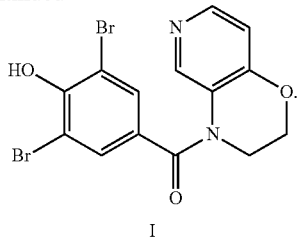

In one embodiment of the present invention, the above steps (1) and (2) can be carried out as an in situ reaction.

In another embodiment of the present invention, the above step of obtaining the compound of Formula III from the compound of Formula II, and the above steps (1) and (2) can be carried out as an in situ reaction.

In another embodiment of the present invention, the compound of Formula IV is obtained by reacting 3,4-dihydro-2H-pyrido[4,3-b][1,4]oxazine with bromic acid in acetic acid.

The present invention also provides an intermediate compound of the following Formula III:

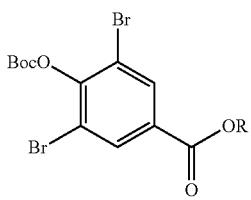

wherein R is hydrogen or Boc.

Furthermore, the present invention provides an intermediate compound of the following Formula IV:

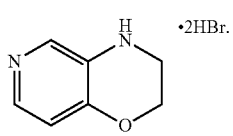

The present invention also provides a pharmaceutical composition for the treatment or prevention of hyperuricemia, gout disease, nephritis, chronic renal failure, nephrolithiasis, uremia, urolithiasis, or a disease associated with uric acid, which comprises as an active ingredient the compound of Formula I, or a pharmaceutically acceptable salt thereof or a hydrate thereof at a dose of greater than 2 mg to 10 mg or less based on the free base of the compound of Formula I and is orally administered once daily.

The present invention also provides the use of the compound of Formula I, or a pharmaceutically acceptable salt thereof or a hydrate thereof for the treatment or prevention of hyperuricemia, gout disease, nephritis, chronic renal failure, nephrolithiasis, uremia, urolithiasis, or a disease associated with uric acid, wherein said compound of Formula I, or a pharmaceutically acceptable salt thereof or a hydrate thereof is orally administered once daily at a dose of greater than 2 mg to 10 mg or less based on the free base of the compound of Formula I.

The present invention also provides a method for treating or preventing hyperuricemia, gout disease, nephritis, chronic renal failure, nephrolithiasis, uremia, urolithiasis, or a disease associated with uric acid in a subject, comprising administering to the subject in need thereof orally once daily the compound of Formula I, or a pharmaceutically acceptable salt thereof or a hydrate thereof at a dose of greater than 2 mg to 10 mg or less based on the free base of the compound of Formula I.

In one embodiment of the present invention, the dose of the compound of Formula I may be 3 mg to 8 mg based on the free base of the compound.

In one embodiment of the present invention, the compound of Formula I may be in the form of hydrochloride of the compound of Formula I or its 1.5 hydrate (sesquihydrate).

The present invention also provides hydrochloride 1.5 hydrate (sesquihydrate) of the compound of Formula I.

In one embodiment of the present invention, the hydrochloride 1.5 hydrate of the compound of Formula I may display characteristic peaks at the following $2\theta$ (two-theta) positions in the powder X-ray diffraction (XRD) analysis:
11.48°±0.5°, 24.11°±0.5°, 24.76°±0.5°, 27.99°±0.5°, 31.43°±0.5°, 34.20°±0.5°.

In one embodiment of the present invention, the hydrochloride 1.5 hydrate of the compound of Formula I may further display characteristic peaks at the following $2\theta$ (two-theta) positions in the powder X-ray diffraction (XRD) analysis:
6.89°±0.5°, 17.61°±0.5°, 21.42°±0.5°, 23.27°±0.5°.

The present invention also provides a process for preparing the hydrochloride 1.5 hydrate of the compound of Formula I, comprising reacting the compound of Formula I with acetic acid, aqueous hydrochloric acid solution and acetone to form crystals.

The present invention also provides a pharmaceutical composition formulated for oral administration, comprising the hydrochloride 1.5 hydrate of the compound of Formula I.

In one embodiment of the present invention, the pharmaceutical composition may be in the form of a tablet.

Effect of the Invention

The process for preparing the heterocycle derivative compound of Formula I according to the present invention solves the problem of generating impurities that are likely to cause carcinogenicity or mutagenesis, by employing instead of the oxazine derivative its stabilized HBr salt (dihydrobromide, 2HBr) form. The process of the present invention also solves another problem of generating toxic intermediates that induce a genetic mutation, by employing a novel benzoic acid intermediate instead of 3,5-dibromo-4-methoxy-benzoyl chloride. Accordingly, the process of the present invention eliminates the need for additional purification steps to remove impurities at each step, which is advantageous for a large-scale production through an in situ reaction.

Furthermore, the dosage regimen according to the present invention in which the compound of Formula I is orally administered once daily at a dose of greater than 2 mg to 10 mg or less shows a remarkably excellent effect in the treatment or prevention of hyperuricemia, gout disease, nephritis, chronic renal failure, nephrolithiasis, uremia, urolithiasis, or a disease associated with uric acid, and minimizes the possibility of side effects.

Furthermore, the previous hydrochloride of the compound of Formula I was problematic in formulating its preparation for oral administration by a wet granulation method due to its hygroscopic property. The hydrochloride 1.5 hydrate of the compound of Formula I according to the present invention solves this problem and exhibits stability suitable for formulations for oral administration (especially tablets).

DETAILED DESCRIPTION

Figure 1:
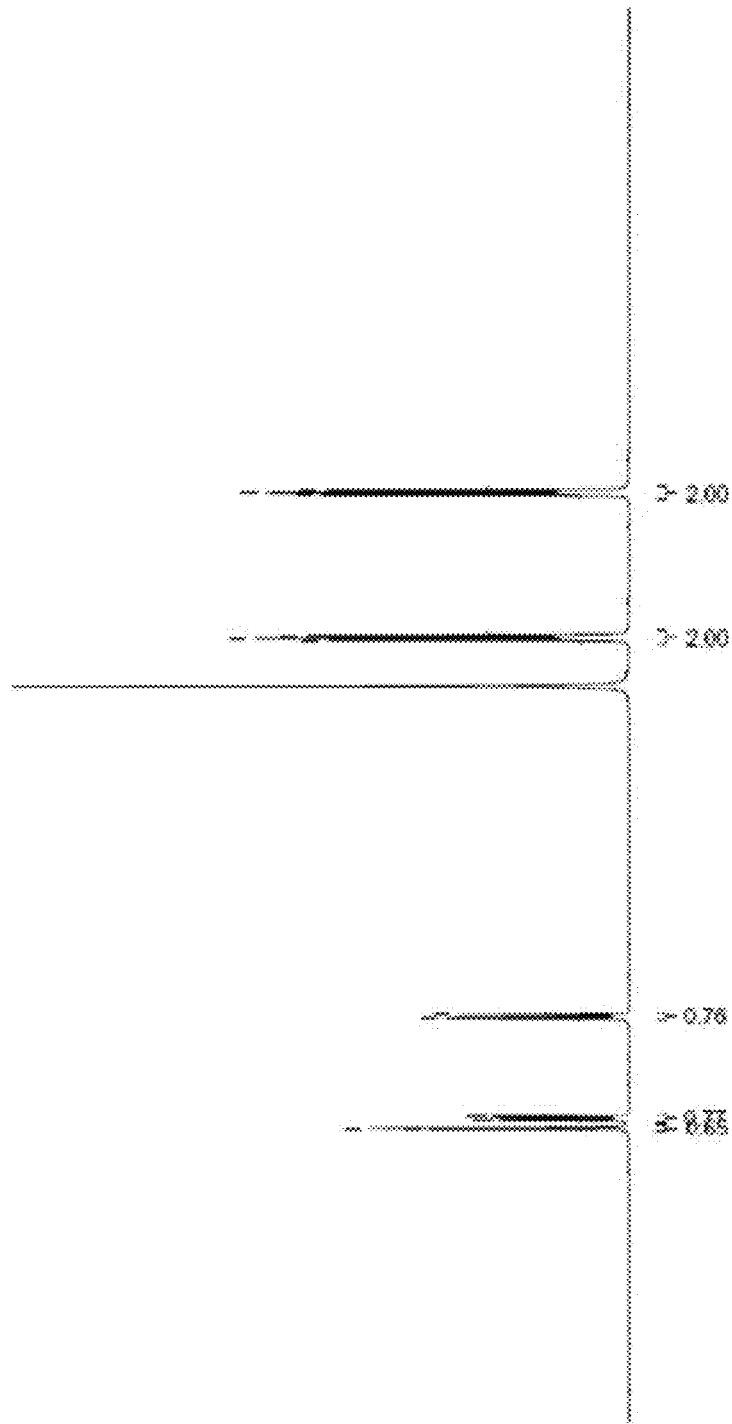
FIG. 1 shows the NMR data of 3,4-dihydro-2H-pyrido[4,3-b][1,4]oxazine HBr salt (dihydrobromide, 2HBr) according to the present invention prepared in Example 1.

Below, the present invention will be explained in more detail.

Process for Preparing the Compound of Formula I, its Salt or Hydrate

The present invention relates to a process for preparing the compound of Formula I, or a pharmaceutically acceptable salt thereof or a hydrate thereof, comprising coupling-reacting a compound of the following Formula III with a compound of the following Formula IV:

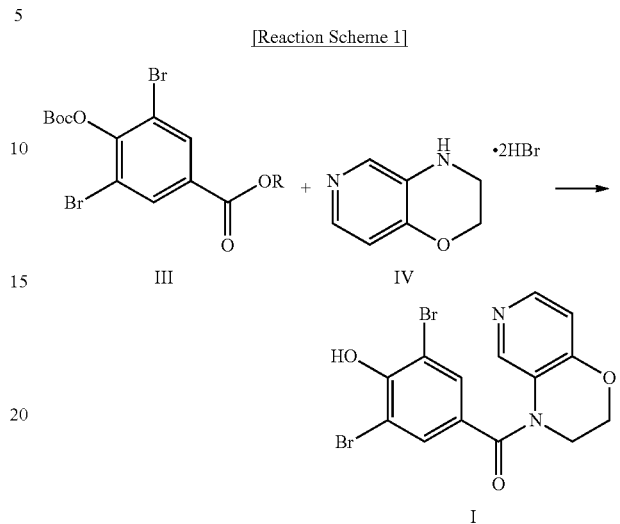

wherein R is hydrogen or Boc.

Specifically, a base is added to the compound of Formula III, and the compound is subject to a coupling reaction with 3,4-dihydro-2H-pyrido[4,3-b][1,4]oxazine HBr salt (2HBr) which is the compound of Formula IV. The resulting intermediate compound is subject to a post-treatment to obtain the compound of Formula I, (3,5-dibromo-4-hydroxyphenyl)(2,3-dihydro-4H-pyrido[4,3-b][1,4]oxazin-4-yl)-methanone or a pharmaceutically acceptable salt thereof.

In one embodiment of the present invention, the compound of Formula III can be obtained by reacting a compound of the following Formula II with di-tert-butyl dicarbonate and pyridine:

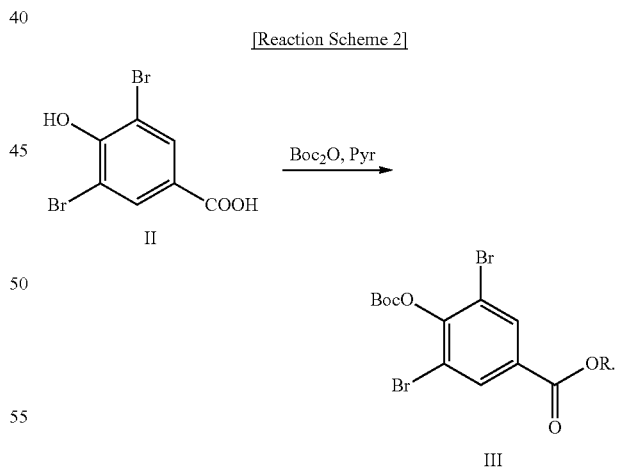

Specifically, a solvent is added to the reactor, and then 3,5-dibromo-4-hydroxybenzoic acid of Formula II is added thereto, di-tert-butyl dicarbonate is added, and pyridine is added, and the reaction is carried out to obtain the compound of Formula III.

The 3,5-dibromo-4-hydroxybenzoic acid, the compound of Formula II, which is used as a low-cost starting material, can be prepared by referencing known methods or can be commercially purchased from a reagent company.

Any conventional solvents that generally do not adversely affect the reaction can be used. Preferable examples of solvents include but are not limited to: ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixed solvent of two solvents selected from the above also can be used. Tetrahydrofuran is preferable for this reaction.

Specifically, tetrahydrofuran (THF) is added to the reactor, and then 3,5-dibromo-4-hydroxybenzoic acid, the compound of Formula II, is added thereto, and di-tert-butyl dicarbonate is added. Pyridine is added under a nitrogen atmosphere, and the reaction is carried out to obtain the compound of Formula III. The reaction can be carried out with stirring at a temperature of 25-30° C. for about 1-3 hours.

The resulting compound of Formula III is a novel benzoic acid intermediate compound. Therefore, the present invention also encompasses the compound of the following Formula III:

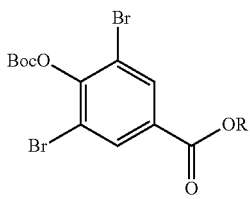

III wherein R is hydrogen or Boc.

The process for preparing the compound of Formula I according to the present invention may comprise the following steps:

(1) reacting the compound of Formula III with the compound of Formula IV to obtain a compound of Formula V;
(2) reacting the compound of Formula V with an alcohol in the presence of an acid to obtain a salt of the compound of Formula I; and
(3) reacting the salt of the compound of Formula I with a base first and then with an acid secondarily:

[Reaction Scheme 3]

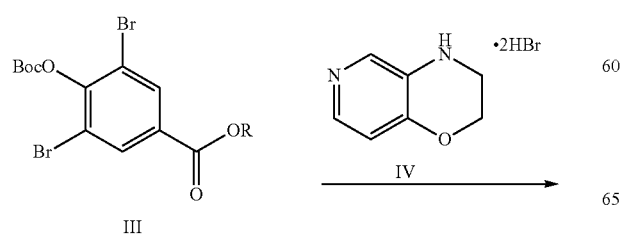

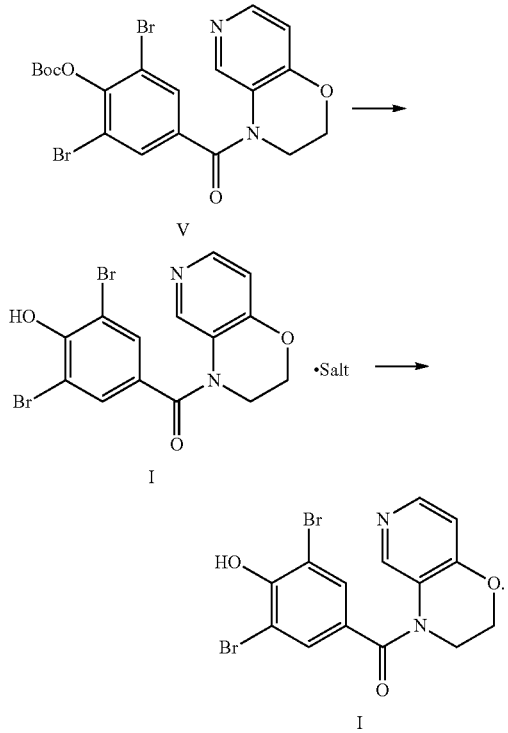

wherein R is hydrogen or Boc.

In one embodiment of the present invention, the process may further comprise a step of reacting the compound of Formula II with di-tert-butyl dicarbonate and pyridine, prior to step (1). In this case, the process for preparing the compound of Formula I can be represented by the following reaction scheme:

[Reaction Scheme 4]

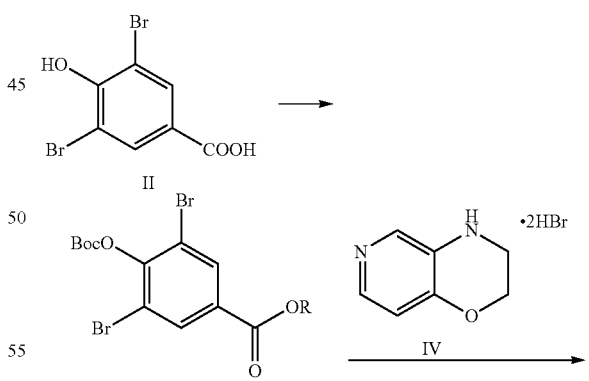

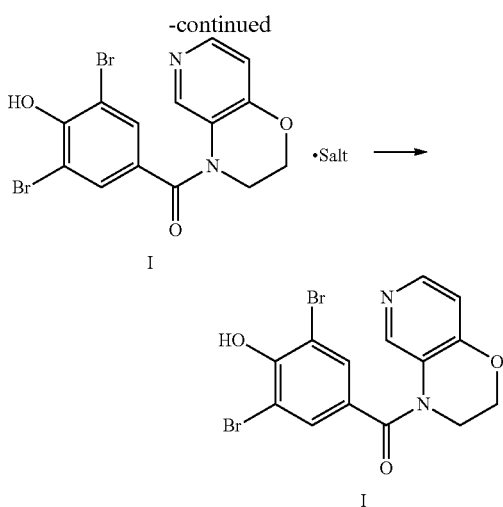

wherein R is hydrogen or Boc.

In one embodiment of the present invention, the above steps (1) and (2) can be carried out as an in situ reaction.

In one embodiment of the present invention, the above step of obtaining the compound of Formula III from the compound of Formula II, and the above steps (1) and (2) can be carried out as an in situ reaction.

The term "in situ reaction" means conducting successive chemical reactions in one reactor, and it is also referred to as a "one-pot reaction." An in situ reaction is very economical and suitable for large-scale production because it allows a following (next) reaction to be carried out immediately without the separation step and the purification step of intermediate compounds.

The preparation process will be explained in more detail below.

Step (1): Reacting the Compound of Formula III With the Compound of Formula IV to Obtain the Compound of Formula V A base is added to the compound of Formula III, and the compound is reacted with 3,4-dihydro-2H-pyrido[4,3-b][1,4]oxazine HBr salt (dihydrobromide, 2HBr) which is the compound of Formula IV.

Examples of base used in the reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc.; and potassium phosphate. Triethylamine is preferable for this reaction.

Specifically, triethylamine is added to the reaction solution, and then 3,4-dihydro-2H-pyrido[4,3-b][1,4]oxazine HBr salt (2HBr) of Formula IV is added to the reaction solution, and the reaction solution is stirred at a temperature of 25-30° C. for about 5-7 hours. After removing the formed salts (precipitate), the filtrate is collected, and then the filtrate is concentrated at a temperature of 25-30° C. to give tert-butyl-(2,6-dibromo-4-(1,2,3,4-tetrahydro-1,7-naphthyridine-1-carbonyl)phenyl)carbonate which is the compound of Formula V.

Step (2): Reacting the Compound of Formula V With an Alcohol in the Presence of an Acid to Obtain a Salt of the Compound of Formula I An alcohol is added to the reactor which contains tert-butyl-(2,6-dibromo-4-(1,2,3,4-tetrahydro-1,7-naphthyridine-1-carbonyl)phenyl)carbonate which is the compound of Formula V, and the mixture is reacted in the presence of an acid to obtain a salt of (3,5-dibromo-4-hydroxyphenyl) (2,3-dihydro-4H-pyrido[4,3-b][1,4]oxazin-4-yl)-methanone.

Examples of acid used in the reaction include inorganic acids such as hydrochloric acid, sulfuric acid, nitric acid, phosphoric acid, hydrobromic acid, hydroiodic acid, etc.; organic carbon acids such as tartaric acid, formic acid, citric acid, acetic acid, trichloroacetic acid or trifluoroacetic acid, gluconic acid, benzoic acid, lactic acid, fumaric acid, maleic acid, etc.; and sulfonic acids such as methanesulfonic acid, benzenesulfonic acid, p-toluenesulfonic acid or naphthalsulfonic acid. Hydrochloric acid is preferable for this reaction.

Examples of alcohol used in the reaction include methanol, ethanol, isopropyl alcohol, tert-butyl alcohol, etc., and isopropyl alcohol is preferable for this reaction.

More specifically, isopropyl alcohol is added to the reactor at a temperature of 25-30° C. which contains tert-butyl-(2,6-dibromo-4-(1,2,3,4-tetrahydro-1,7-naphthyridine-1-carbonyl)phenyl)carbonate which is the compound of Formula V, and then concentrated hydrochloric acid is slowly added at 45° C. or lower. The reaction solution is cooled to 25-30° C. and stirred for about 1-2 hours. Isopropyl alcohol is added to the reaction solution at 25-30° C. and further stirred for about 1 hour, and then the reaction solution is cooled to 20-25° C. The resulting crystals are filtered and dried to give (3,5-dibromo-4-hydroxyphenyl)(2,3-dihydro-4H-pyrido[4,3-b][1,4]oxazin-4-yl)methanone hydrochloride.

Step (3): Reacting the Salt of the Compound of Formula I with a Base First and then With an Acid Secondarily to Obtain the Compound of Formula I Water is added to a clean reactor, and the salt of 3,5-dibromo-4-hydroxyphenyl)(2,3-dihydro-4H-pyrido[4,3-b][1,4]oxazin-4-yl)methanone is added to the reactor, and then the solution is reacted with a base and an acid successively. The resulting crystals are filtered to obtain (3,5-dibromo-4-hydroxyphenyl)(2,3-dihydro-4H-pyrido[4,3-b][1,4]oxazin-4-yl)-methanone which is the compound of Formula I.

Examples of base used in the reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc.; and potassium phosphate. Sodium hydroxide is preferable for this reaction.

Examples of acid used in the reaction include inorganic acids such as hydrochloric acid, sulfuric acid, nitric acid, phosphoric acid, hydrobromic acid, hydroiodic acid, etc.; organic carbon acids such as tartaric acid, formic acid, citric acid, acetic acid, trichloroacetic acid or trifluoroacetic acid, gluconic acid, benzoic acid, lactic acid, fumaric acid, maleic acid, etc.; and sulfonic acids such as methanesulfonic acid, benzenesulfonic acid, p-toluenesulfonic acid or naphthalsulfonic acid. Hydrochloric acid is preferable for this reaction.

More specifically, water is added to a clean reactor, and the (3,5-dibromo-4-hydroxyphenyl)(2,3-dihydro-4H-pyrido[4,3-b][1,4]oxazin-4-yl)methanone hydrochloride obtained in the above step (2) is added to the reactor at 25-30° C., and then the reaction solution is stirred at 25-30° C. for about 15 minutes. The aqueous sodium hydroxide solution is slowly added at 25-30° C. until the pH reaches 10.0, and the reaction solution is filtered, and the filtrate is collected. Ethyl acetate is added to the reactor and stirred to separate the aqueous layer, and the aqueous hydrochloric acid solution is added at 20-25° C. until the pH reaches 6.4 to 6.7. The resulting crystals are filtered to obtain (3,5-dibromo-4-hydroxyphenyl)(2,3-dihydro-4H-pyrido[4,3-b][1,4]oxazin-4-yl)-methanone which is the compound of Formula I.

The process for preparing the compound of Formula I as explained above will be described in more detail in the following working examples.

Process for Preparing the Compound of Formula IV

In one embodiment of the present invention, the compound of Formula IV can be produced by a preparation method that comprises a step of reacting 3,4-dihydro-2H-pyrido[4,3-b][1,4]oxazine with bromic acid in acetic acid.

In another embodiment of the present invention, the compound of Formula IV can be produced by the following steps:

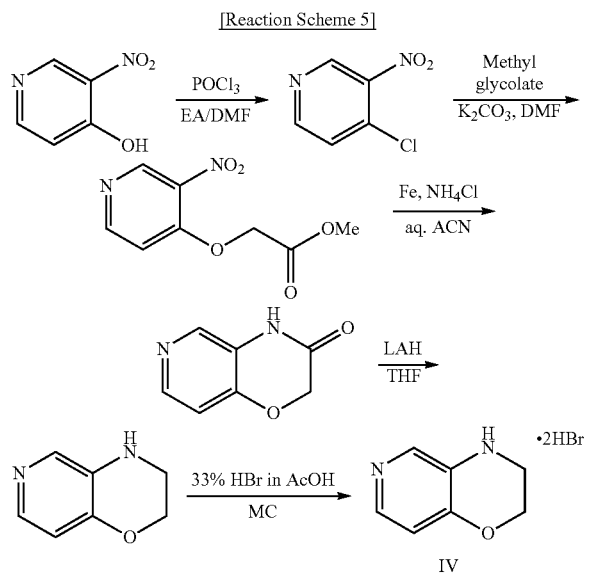

Specifically, the above preparation method is as follows.
(1) Phosphoryloxy chloride is added to 4-hydroxy-nitropyridine to obtain 4-chloro-3-nitropyridine.
(2) Methylglycolate and potassium carbonate are added to 4-chloro-3-nitropyridine to obtain methyl 2-((3-nitropyridin-4-yl)oxy)acetate.
(3) Ammonium chloride (NH$_4$Cl) and iron (Fe) are added to methyl 2-((3-nitropyridin-4-yl)oxy)acetate to obtain 2H-pyrido[4,3-b][1,4]oxazin-3(4H)-one.
(4) Lithium aluminum hydride (LiAlH$_4$, LAH) is added to 2H-pyrido[4,3-b][1,4]oxazin-3(4H)-one to obtain 3,4-dihydro-2H-pyrido[4,3-b][1,4]oxazine.
(5) Bromic acid in acetic acid is added to 3,4-dihydro-2H-pyrido[4,3-b][1,4]oxazine to finally obtain 3,4-dihydro-2H-pyrido[4,3-b][1,4]oxazine HBr salt (2HBr) which is the compound of Formula IV.

Therefore, the present invention also encompasses a novel intermediate compound of the following Formula IV:

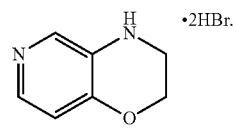

IV

The process for preparing the intermediate compound of Formula IV as explained above will be described in more detail in the following working examples.

Use of the Compound of Formula I

Furthermore, the present invention relates to a pharmaceutical composition for the treatment or prevention of hyperuricemia, gout disease, nephritis, chronic renal failure, nephrolithiasis, uremia, urolithiasis, or a disease associated with uric acid, which comprises as an active ingredient the compound of Formula I, or a pharmaceutically acceptable salt thereof or a hydrate thereof at a dose of greater than 2 mg to 10 mg or less based on the free base of the compound of Formula I and is orally administered once daily.

Furthermore, the present invention relates to the use of the compound of Formula I, or a pharmaceutically acceptable salt thereof or a hydrate thereof for the treatment or prevention of hyperuricemia, gout disease, nephritis, chronic renal failure, nephrolithiasis, uremia, urolithiasis, or a disease associated with uric acid, wherein said compound of Formula I, or a pharmaceutically acceptable salt thereof or a hydrate thereof is orally administered once daily at a dose of greater than 2 mg to 10 mg or less based on the free base of the compound of Formula I.

Furthermore, the present invention relates to a method for treating or preventing hyperuricemia, gout disease, nephritis, chronic renal failure, nephrolithiasis, uremia, urolithiasis, or a disease associated with uric acid in a subject, comprising administering to the subject in need thereof orally once daily the compound of Formula I, or a pharmaceutically acceptable salt thereof or a hydrate thereof at a dose of greater than 2 mg to 10 mg or less based on the free base of the compound of Formula I.

In one embodiment of the present invention, the compound of Formula I, which is included as an active ingredient in the pharmaceutical composition, the use and the method, may be in the form of a pharmaceutically acceptable salt or hydrate thereof.

The pharmaceutically acceptable salts may include acid addition salts prepared by acids that form non-toxic acid addition salts containing pharmaceutically acceptable anions—for example, inorganic acids such as hydrochloric acid, sulfuric acid, nitric acid, phosphoric acid, hydrobromic acid, hydroiodic acid, etc.; organic carbon acids such as tartaric acid, formic acid, citric acid, acetic acid, trichloroacetic acid or trifluoroacetic acid, gluconic acid, benzoic acid, lactic acid, fumaric acid, maleic acid, etc.; and sulfonic acids such as methanesulfonic acid, benzenesulfonic acid, p-toluenesulfonic acid or naphthalsulfonic acid. Salts with alkali metal such as sodium, potassium or the like are also included. In addition, salts with other acids or bases that are known and conventionally used in the technical field pertaining to aromatic amidine derivatives or lactam derivatives, may be included. Furthermore, the hydrate forms may include hemihydrate, monohydrate, 1.5 hydrate (sesquihydrate), dihydrate, trihydrate and the like.

Specifically, the pharmaceutically acceptable salt may be hydrochloride, and the hydrate may be 1.5 hydrate.

Hyperuricemia is the abnormally high level of uric acid in blood. It is defined as a condition wherein the serum uric acid level is higher than normal (7~8 mg/dl for males, 6 mg/dl for females) due to under-excretion of uric acid in the kidney or overproduction of uric acid in the liver. Gout disease has a remarkably higher level uric acid in blood than normal (7~8 mg/dl for males, 6 mg/dl for females) due to overproduction of uric acid or under-excretion of uric acid. Uric acid crystals can be deposited on connective soft tissues such as joints and ligaments, and needle-like uric acid crystals can prick (stick) muscles around the joints. Then, the body's immune system attacks uric acid crystals, which causes severe pain and swelling around the joints. Such paroxysmal and inflammatory forms of arthritis are called gout. The uric acid crystals are deposited mainly in the metatarsophalangeal joint of the big toe, and rarely in the lumbar spine [Vervaeck M., et al., Clinical Neurology and Neurosurgery, 93, p 233-236 (1991)].

Gout is a very dangerous factor because it may cause a complication of various metabolic diseases such as diabetes, hypertension, heart disease, obesity, nephrolithiasis, urolithiasis and the like. Peak incidence of gout is observed predominantly in males in age of 40's to 50's and increases in postmenopausal female patients. Also, the onset frequency is high in obese persons and those who engage in very vigorous exercise.

Incidence of gouty attack is closely associated with patients who have had hyperuricemia for years. It has been reported that incidence of gouty attack is 4.9% when uric acid level in the body is 9 mg/dl or higher, 0.5% when uric acid level in the body is 7.0-8.9 mg/dl and 0.1% when uric acid level in the body is 7.0 mg/dl or lower, and accumulated incidence of gouty attack for 5 years is about 22% in patients having uric acid level in the body of 9 mg/dl or higher [Campion E. W. et al., Am. J. Med., 82, p 421-426 (1987)].

Reducing the serum uric acid (UA) level below <6.0 mg/dL, more preferably below <5.0 mg/dL, is clinically significant for the treatment of patients with severe gout. The dosage regimen according to the present invention in which the compound of Formula I, or a pharmaceutically acceptable salt thereof or a hydrate thereof is orally administered once daily at a dose of greater than 2 mg to 10 mg or less based on the free base of the compound of Formula I, has a significant effect in reducing the patient's serum uric acid level to below <5.0 mg/dL.

Figure 13:
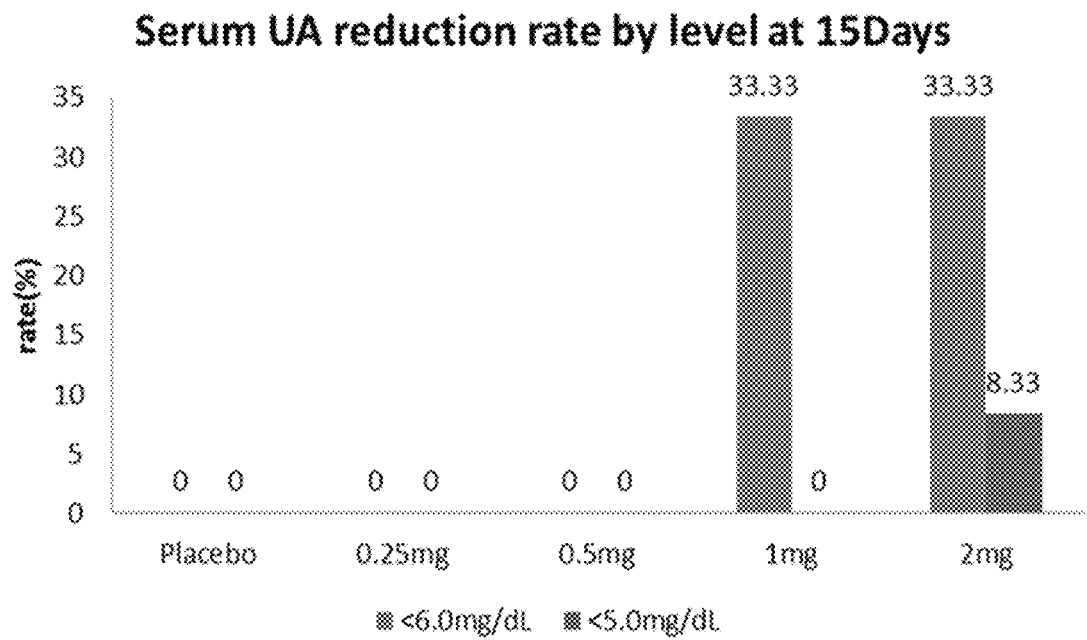
FIG. 13 shows the percentage of patients whose serum uric level fell below <5.0 mg/dL (right bar) and the percentage of patients whose serum uric level fell below <6.0 mg/dL (left bar) upon administration of the compound of Formula I according to the present invention at low doses (0.25 mg, 0.5 mg, 1 mg) and at a dose of 2 mg.
Figure 14:
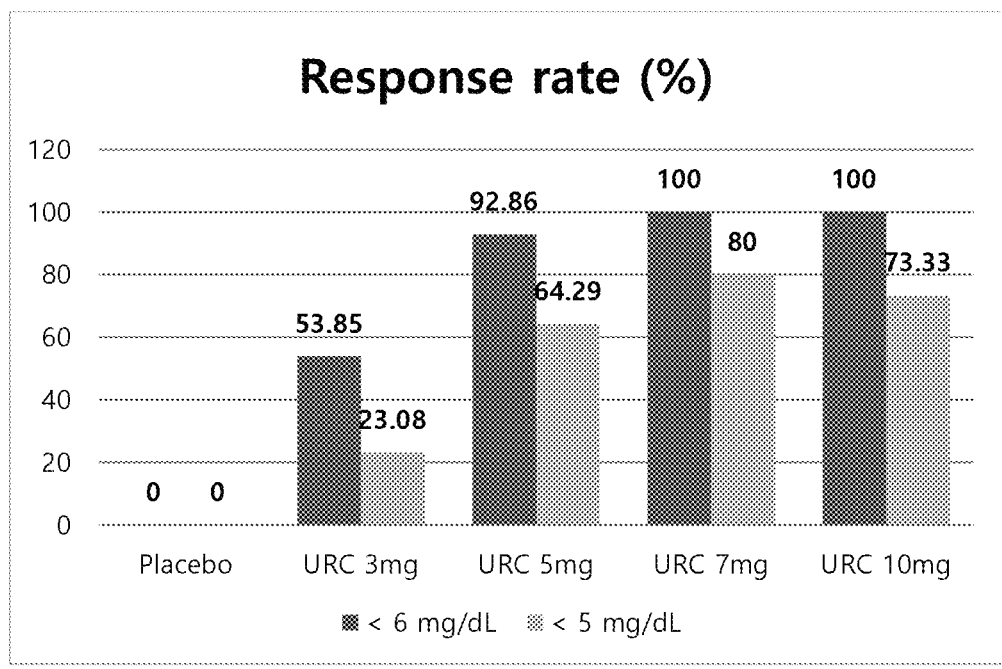
FIG. 14 shows the percentage of patients whose serum uric level fell below <5.0 mg/dL (right bar) and the percentage of patients whose serum uric level fell below <6.0 mg/dL (left bar) upon administration of the compound of Formula I according to the present invention at doses within the claimed dosage regimen (3 mg, 5 mg, 7 mg, 10 mg).

Specifically, as can be seen in Experimental Example 4 to be described below, in the case of administration of 3 mg, 5 mg, 7 mg and 10 mg according to the dosage regimen of the present invention, the percentages of patients whose serum uric acid level fell below <5.0 mg/dL were approximately 23%, 64%, 80% and 73%, respectively, in other words, in the range of about 23% to 80% (see FIG. 14). However, in the case of administration of the same compound at doses of 0.25 mg, 0.5 mg and 1 mg, no patient showed the serum uric acid level below <5.0 mg/dL, and only in the case of 2 mg dose the percentage was merely about 8% (see FIG. 13). From the above experimental results, it can be understood that a significant effect occurs at a dose greater than 2 mg which is the lower limit of the dose range of the dosage regimen according to the present invention.

Furthermore, the dosage regimen according to the present invention in which the compound of Formula I is orally administered once daily at a dose of greater than 2 mg to 10 mg or less shows a potent inhibitory activity on human urate anion transporter 1 (hURAT1), and thus it is useful for the treatment or prevention of hyperuricemia, gout disease such as acute gouty arthritis, chronic gouty arthritis, gouty nodules and gouty nephropathy; nephritis, chronic renal failure, nephrolithiasis, uremia, urolithiasis, and a disease associated with uric acid, such as hyperlipidemia, ischemic heart disease, myocardial infarction, cerebral infarction, cerebrovascular disease, diabetes, hypertension and the like.

In one embodiment of the present invention, the dose of the compound of Formula I may vary depending on the disease, condition, age, body weight of the patient and the dosage form within the range of greater than 2 mg to 10 mg or less by oral administration once daily. Specifically, the compound can be orally administered once daily at a dose of 3 mg to 8 mg, and more specifically, once daily at a dose of 3 mg to 6 mg. The above dose range is based on the free base form of the compound of Formula I which is the active ingredient, and the compound of Formula I can be administered in the form of hydrochloride or its 1.5 hydrate form. Specifically, when the compound of Formula I is administered in its hydrochloride 1.5 hydrate form, the dose may be greater than 2.3 mg to 11.5 mg or less.

At doses equal to or less than 2 mg, no sufficient effect is exerted for the treatment of the above-mentioned diseases. At a dose of 10 mg, the maximum effect is already exhibited. In addition, while doses of above 10 mg show an effect of decreasing the uric acid concentration, such doses can induce arthralgia, joint swelling and the like during the process of treatment which can cause pain in the patient, and there is a possibility of other side effects. These side effects include increased levels of creatinine, which can cause fatal diseases, especially in the kidneys. As can be seen in Experimental Example 5 to be described below, it can be inferred that when the dose exceeds 10 mg which is the maximum dose of the dosage regimen of the present invention, there is a greater risk of an increased incidence of adverse events such as arthralgia and joint swelling, and increased urinary creatinine concentration.

The subject of the use according to the present invention is an animal, preferably a mammal, most preferably a human.

Hydrochloride 1.5 Hydrate of the Compound of Formula I

The present invention also relates to hydrochloride 1.5 hydrate (sesquihydrate) of the compound of Formula I.

The present invention also provides a process for preparing the hydrochloride 1.5 hydrate of the compound of Formula I, comprising reacting the compound of Formula I with acetic acid, aqueous hydrochloric acid solution and acetone to form crystals.

Specifically, the compound of Formula I, (3,5-dibromo-4-hydroxyphenyl)(2,3-dihydro-4H-pyrido[4,3-b][1,4] oxazin-4-yl)-methanone, is placed in a reactor at 25° C., acetic acid is immediately added thereto at the same temperature, and water is added to the reactor. After adding an aqueous hydrochloric acid solution to the reactor at 25° C., acetone is added to the reaction solution to form crystals, and the resulting crystals are filtered and vacuum dried to obtain (3,5-dibromo-4-hydroxyphenyl)(2,3-dihydro-4H-pyrido[4,3-b][1,4]oxazin-4-yl)-methanone hydrochloride 1.5 hydrate.

The process for preparing the hydrochloride 1.5 hydrate of the compound of Formula I as explained above will be described in more detail in the following working examples.

In one embodiment of the present invention, the hydrochloride 1.5 hydrate of the compound of Formula I may display characteristic peaks at the following 2θ (two-theta) positions in the powder X-ray diffraction (XRD) analysis:
11.48°±0.5°, 24.11°±0.5°, 24.76°±0.5°, 27.99°±0.5°, 31.43°±0.5°, 34.20°±0.5°.

In one embodiment of the present invention, the hydrochloride 1.5 hydrate of the compound of Formula I may further display characteristic peaks at the following 2θ (two-theta) positions in the powder X-ray diffraction (XRD) analysis:

6.89°±0.5°, 17.61°±0.5°, 21.42°±0.5°, 23.27°±0.5°.

In one embodiment of the present invention, the hydrochloride 1.5 hydrate of the compound of Formula I may display characteristic peaks at the following 2θ (two-theta) positions in the powder X-ray diffraction (XRD) analysis:
6.89°±0.5°, 10.84°±0.5°, 11.48°±0.5°, 13.73°±0.5°, 15.85°±0.5°, 17.61°±0.5°, 18.51°±0.5°, 19.98°±0.5°, 21.42°±0.5°, 22.99°±0.5°, 23.27°±0.5°, 24.11°±0.5°, 24.76°±0.5°, 27.37°±0.5°, 27.99°±0.5°, 31.43°±0.5°, 34.20°±0.5°.

Furthermore, the present invention relates to a pharmaceutical composition formulated for oral administration, comprising the hydrochloride 1.5 hydrate of the compound of Formula I.

The pharmaceutical composition according to the present invention can be prepared by mixing an effective amount of the hydrochloride 1.5 hydrate of the compound of Formula I as an active ingredient with a pharmaceutically acceptable carrier, vehicle, binder, stabilizer and/or diluent. The pharmaceutical composition according to the present invention may be manufactured as a unit dosage form or included in a multi-dose container by formulation with pharmaceutically acceptable carriers and/or excipients according to a method that could be easily carried out by those skilled in the art. Pharmaceutically acceptable carriers may be solid or liquid and may be one or more selected from excipients, antioxidants, buffers, bacteriostats, dispersants, adsorbents, surfactants, binders, preservatives, disintegrants, sweeteners, flavors, glidants, release-controlling agents, wetting agents, stabilizers, suspending agents and lubricants. In addition, the pharmaceutically acceptable carriers may be selected from saline solution, sterilized water, Ringer's solution, buffered saline, dextrose solution, maltodextrin solution, glycerol, ethanol and mixtures thereof.

The pharmaceutical composition according to the present invention can be prepared in forms of pharmaceutical formulation suitable for oral administration. The above pharmaceutical preparations can be administered orally in form of powder, granule, tablet, capsule, syrup or suspension, and specifically they may be in the form of tablets. Also, in one embodiment, the above pharmaceutical preparation may be formulated so as to coat the active ingredient or protect it from degradation in the stomach.

Hereinafter, the present invention will be explained in more detail through working examples. However, the following working examples are only intended to illustrate one or more embodiments and are not intended to limit the scope of the invention.

EXAMPLES

Example 1

Synthesis of 3,4-dihydro-2H-pyrido[4,3-b][1,4] oxazine HBr salt (dihydrobromide, 2HBr) Which is the Compound of Formula IV (1) Preparation of 4-chloro-3-nitropyridine 50 g (0.356 mmol) of 4-hydroxy-nitropyridine was added to 50 mL (1 T) of DMF (dimethylformamide) and 450 mL (9 T) of ethyl acetate, and stirred. 42.5 mL of phosphoryloxy chloride ($POCl_3$, 1.3 eq) was added thereto, and the mixture was heated and refluxed at 70-80° C. for 2 hours. After completion of the reaction, the reaction solution was cooled to 40° C. and 200 mL of water was added to terminate the reaction. The separated organic layer was washed with 200 mL of saturated sodium bicarbonate ($NaHCO_3$) and 200 mL of brine, respectively, and the collected organic layer was dried over magnesium sulfate ($MgSO_4$), filtered, and concentrated under reduced pressure to obtain 60 g of concentrated crystals of 4-chloro-3-nitropyridine in pale yellow color.

(2) Preparation of methyl 2-((3-nitropyridin-4-yl)oxy)acetate 60 g (0.356 mmol) of 4-chloro-3-nitropyridine obtained in the above step (1) was dissolved in 300 mL (5 T) of DMF, and 36 mL (1.3 eq) of methyl glycolate and 74 g (1.5 eq) of potassium carbonate ($K_2CO_3$) powder were added thereto, and the mixture was heated and reacted at 70-80° C. for 1-2 hours. After completion of the reaction, the reaction mixture was cooled to room temperature, dissolved and neutralized by adding 150 mL of 10% HCl, and extracted with 500 mL of ethyl acetate. The obtained organic layer was washed with 150 mL of brine, and the obtained organic layer was concentrated under reduced pressure and vacuum dried to obtain 62 g (82%) of methyl 2-((3-nitropyridin-4-yl)oxy) acetate in pale brown solid.

(3) Preparation of 2H-pyrido[4,3-b][1,4]oxazin-3(4H)-one 62 g (0.291 mmol) of methyl 2-((3-nitropyridin-4-yl)oxy) acetate obtained in the above step (2) was dissolved in 480 mL of acetonitrile (ACN) and 120 mL of water ($H_2O$), and 16 g (1.0 eq) of ammonium chloride ($NH_4Cl$) and 33 g (2.0 eq) of iron (Fe) powder were added thereto, and the mixture was heated and reacted at 70-80° C. for 2 hours. After completion of the reaction, the reaction mixture was cooled to room temperature, 30 mL of conc-HCl was added thereto, and the mixture was stirred for 30 minutes. The reaction solution was filtered to remove the insoluble substances. The resulting reaction solution was concentrated until a solid was generated. The concentrate was added in methanol, stirred and filtered to obtain 2H-pyrido[4,3-b][1,4]oxazin-3(4H)-one hydrochloride. The same was dissolved in water and then neutralized with 10% sodium hydroxide (NaOH) (pH 6-7), and the resulting solid was filtered and dried to obtain 2H-pyrido[4,3-b][1,4]oxazine-3(4H)-one.

$^1$H-NMR (300 MHz, MeOD-d): δ=8.06 (m, 2H), 6.97 (s, 1H), 4.72 (s, 2H).

(4) Preparation of 3,4-dihydro-2H-pyrido[4,3-b][1,4] oxazine 38 g (0.251 mmol) of 2H-pyrido[4,3-b][1,4]oxazin-3 (4H)-one obtained in the above step (3) was dissolved in 570 mL of tetrahydrofuran (THF) (15 T), and the temperature of the reaction solution was cooled to 0° C. 15 g (1.5 eq) of lithium aluminum hydride ($LiAlH_4$, LAH) was added thereto several times, and the reaction solution was warmed to room temperature and stirred for 2 hours. After completion of the reaction, the mixture was cooled to 0° C., 40 mL of $H_2O$ was slowly added dropwise, and the mixture was stirred for 10 minutes. 80 mL of 5% NaOH solution was added dropwise and the mixture was stirred for 30 minutes at room temperature. The reaction solution was filtered to remove $Al(OH)_3$ insoluble substances. The filtrate was neutralized (pH 7) with 10% HCl, extracted with ethyl acetate, and the organic layer was washed with brine, and dried over anhydrous sodium sulfate ($Na_2SO_4$) and filtered. The filtrate was concentrated under reduced pressure to obtain 3,4-dihydro-2H-pyrido[4,3-b][1,4]oxazine (30 g, 90%).

(5) Preparation of 3,4-dihydro-2H-pyrido[4,3-b][1,4] oxazine HBr salt (2HBr)

100 g (0.666 mol) of 2H-pyrido[4,3-b][1,4]oxazin-3(4H)-one was stirred in 570 mL of THF (15 T), and the temperature of the reaction solution was cooled to 0° C. 38 g (0.999 mol, 1.5 eq) of lithium aluminum hydride ($LiAlH_4$, LAH) was added thereto several times, and the reaction solution was warmed to room temperature and stirred for 2 hours. After completion of the reaction, the reaction mixture was cooled and quenched at 0° C., filtered and concentrated, stirred with MC (methylene chloride) and filtered. The MC used herein was 1,000 mL (10 v/w) of 2H-pyrido[4,3-b][1,4]oxazin-3 (4H)-one. To the 3,4-dihydro-2H-pyrido[4,3-b][1,4]-oxazine/MC solution was added bromic acid in 294 g (210 mL) of 33% acetic acid (d, 1.40 g/mL), which corresponds to 1.8 equivalents (based on 2H-pyrido[4,3-b][1,4]-oxazine-3(4H)-one, 1.199 mmol), in dropwise at 20-30° C. for 20-30 minutes. The resulting crystalline solution was stirred at room temperature for 1 hour, cooled to 5-10° C., and then stirred for another 30 minutes. The crystalline solution was filtered, washed with 300-500 mL of MC and vacuum dried for 5 hours at room temperature to give 95% yield of 3,4-dihydro-2H-pyrido[4,3-b][1,4]oxazine HBr salt (2HBr) which is the compound of the following Formula IV:

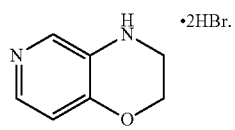

IV

Figure 2:
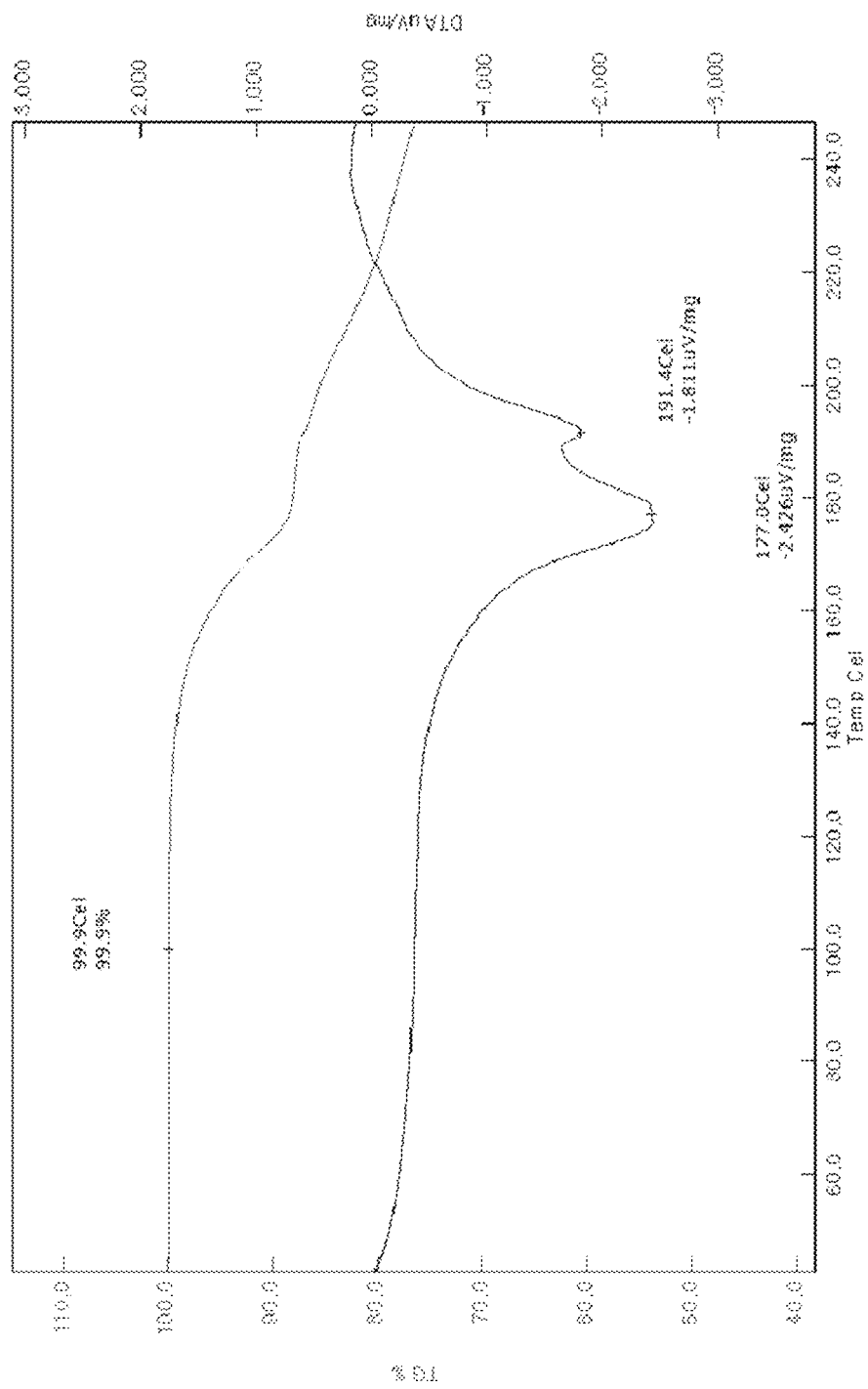
FIG. 2 shows the thermogravimetric (TG)/differential thermal analysis (DTA) results of 3,4-dihydro-2H-pyrido[4,3-b][1,4]oxazine HBr salt (2HBr) according to the present invention prepared in Example 1.

The NMR data of the above compound are shown in FIG. 1, and the thermogravimetric (TG)/differential thermal analysis (DTA) results of the same compound are shown in FIG. 2.

Example 2

Synthesis of (3,5-dibromo-4-hydroxyphenyl)(2,3-dihydro-4H-pyrido[4,3-b][1,4]oxazin-4-yl)-methanone Which is the Compound of Formula I 1 L of tetrahydrofuran (THF) was added to a reactor at 25-30° C., and then 139 g (0.470 mol) of 3,5-dibromo-4-hydroxybenzoic acid was added thereto, and 278 g (1.27 mol) of di-tert-butyl dicarbonate was added to the reactor. 125 g (1.58 mol) of pyridine was added under a nitrogen atmosphere, and the reaction solution was stirred at 25-30° C. for 2 hours to obtain a reaction solution that contains 3,5-dibromo-4-tert-butoxycarbonyloxy-benzoic acid and 3,5-dibromo-4-((tert-butoxycarbonyl)oxy)benzoic(tert-butylcarbonyl) anhydride.

To the above reaction solution was added 170 g (1.68 mol) of triethylamine at a temperature of 25-30° C., and 100 g of 3,4-dihydro-2H-pyrido[4,3-b][1,4]oxazine HBr salt (2HBr) prepared in Example 1 above was added thereto. The reaction solution was stirred at 25-30° C. for 6 hours. After removing the formed salts (precipitate), the filtrate was collected and concentrated at a temperature of 25-30° C. to obtain tert-butyl-(2,6-dibromo-4-(1,2,3,4-tetrahydro-1,7-naphthyridine-1-carbonyl)phenyl)carbonate.

500 mL of isopropyl alcohol was added to the reactor at a temperature of 25-30° C. which contains tert-butyl-(2,6-dibromo-4-(1,2,3,4-tetrahydro-1,7-naphthyridine-1-carbonyl)phenyl)carbonate, and then 500 mL of concentrated hydrochloric acid was slowly added thereto at 45° C. or lower. The reaction solution was cooled to 25-30° C. and stirred for 1-2 hours. 3 L of isopropyl alcohol was added to the reaction solution at 25-30° C. and further stirred for another 1 hour, and then the reaction solution was cooled to 20-25° C. The resulting crystals were filtered and dried to give (3,5-dibromo-4-hydroxyphenyl)(2,3-dihydro-4H-pyrido[4,3-b][1,4]oxazin-4-yl)methanone hydrochloride.

Figure 3:
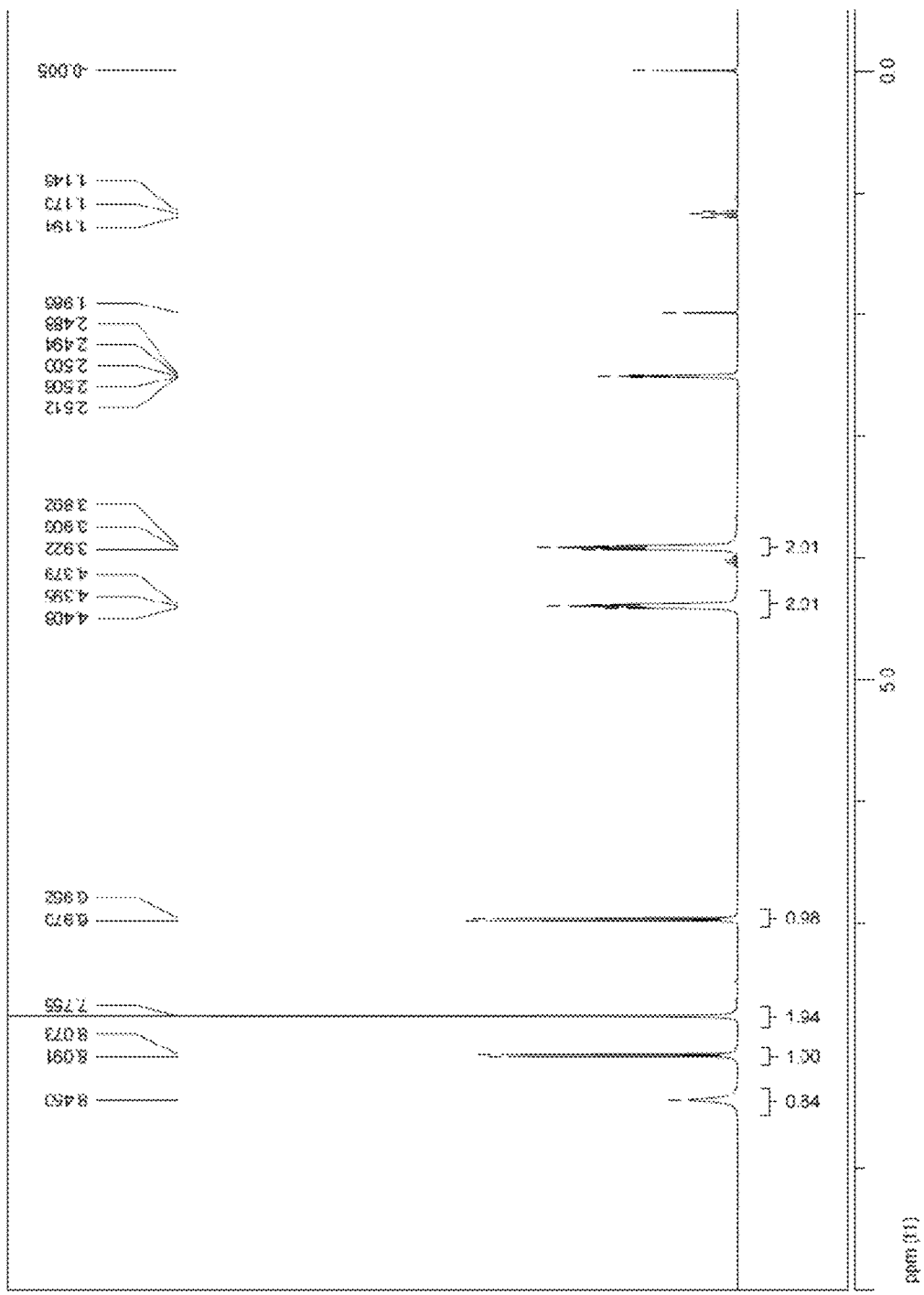
FIG. 3 shows the NMR data of the compound of Formula I according to the present invention prepared in Example 2.

Water was added to a clean reactor, and the (3,5-dibromo-4-hydroxyphenyl)(2,3-dihydro-4H-pyrido[4,3-b][1,4]oxazin-4-yl)methanone hydrochloride obtained in the above was added to the reactor at 25-30° C., and then the reaction solution was stirred at 25-30° C. for 15 minutes. 100 mL of 4N aqueous sodium hydroxide solution was slowly added at 25-30° C. until the pH reached 10.0, and the reaction solution was filtered, and the filtrate was collected. Ethyl acetate was added to the reactor and stirred to separate the aqueous layer, and 10% aqueous hydrochloric acid solution was added at 20-25° C. until the pH reached 6.4 to 6.7. The resulting crystals were filtered to obtain (3,5-dibromo-4-hydroxyphenyl)(2,3-dihydro-4H-pyrido[4,3-b][1,4]oxazin-4-yl)-methanone which is the compound of Formula I (yield: 60%, purity: 98.0% or more). The NMR data of the above compound are shown in FIG. 3.

Example 3

Synthesis of (3,5-dibromo-4-hydroxyphenyl)(2,3-dihydro-4H-pyrido[4,3-b][1,4]oxazin-4-yl)-methanone hydrochloride 1.5 hydrate 83 g of (3,5-dibromo-4-hydroxyphenyl)(2,3-dihydro-4H-pyrido[4,3-b][1,4]oxazin-4-yl)-methanone prepared in Example 2 above was placed in a reactor at 25° C., and 584 mL of acetic acid was immediately added thereto at the same temperature, and 83 mL of water was added to the reactor. After adding 111 mL of 2M aqueous hydrochloric acid solution to the reactor at 25° C., 688 mL of acetone was added to the reaction solution to form crystals, and the resulting crystals were filtered and vacuum dried for 12 hours to obtain (3,5-dibromo-4-hydroxy-phenyl)(2,3-dihydro-4H-pyrido[4,3-b][1,4]oxazin-4-yl)-methanone hydrochloride 1.5 hydrate (yield: 90%, purity: 99.9%).

Figure 4:
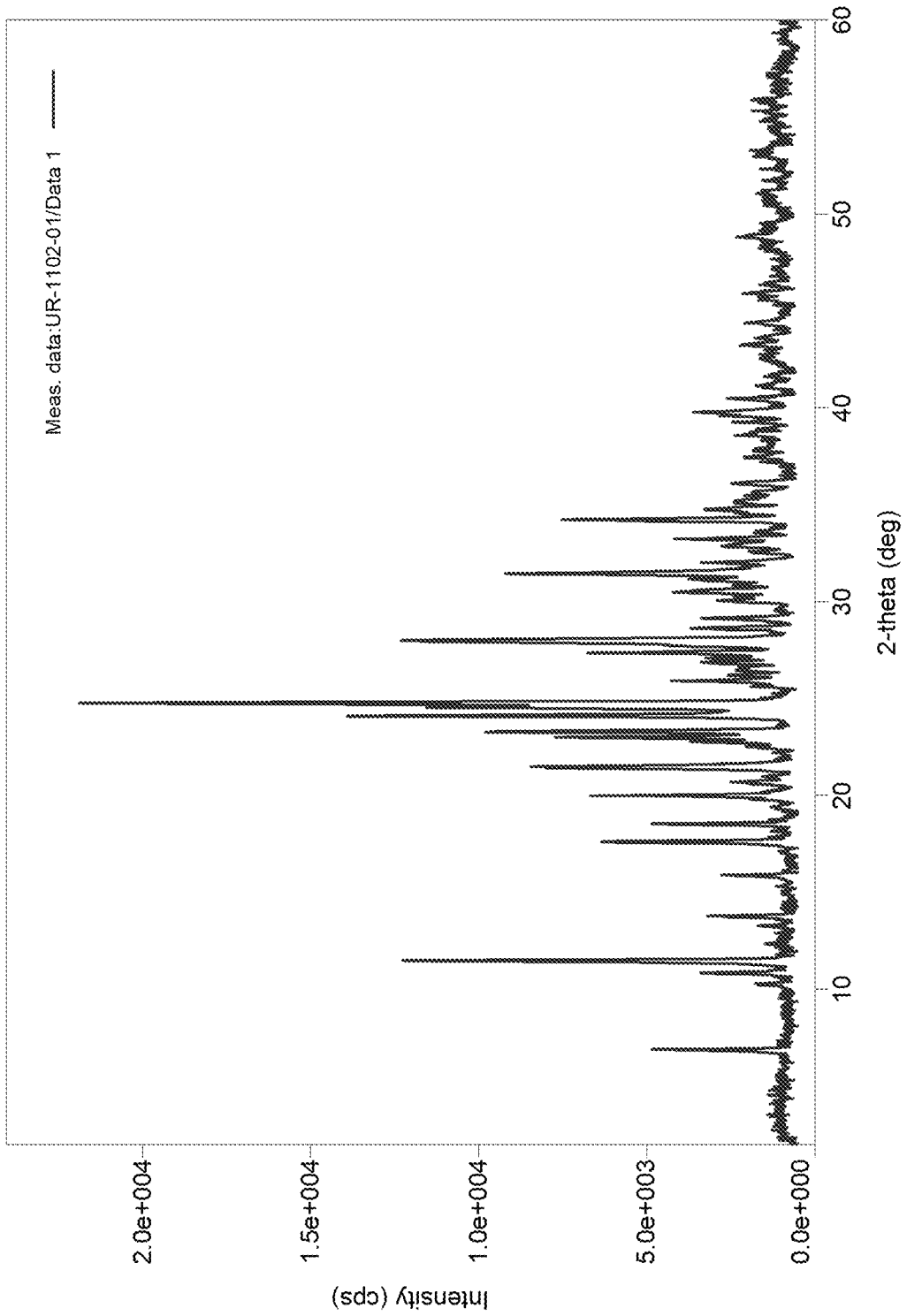
FIG. 4 shows the powder X-ray diffraction (XRD) analysis results of the hydrochloride 1.5 hydrate of the compound of Formula I according to the present invention prepared in Example 3.

The powder X-ray diffraction (XRD) analysis results of the obtained (3,5-dibromo-4-hydroxy-phenyl)(2,3-dihydro-4H-pyrido[4,3-b][1,4]oxazin-4-yl)-methanone hydrochloride 1.5 hydrate are shown in FIG. 4. As shown in FIG. 4, (3,5-dibromo-4-hydroxy-phenyl)(2,3-dihydro-4H-pyrido[4,3-b][1,4]oxazin-4-yl)-methanone hydrochloride 1.5 hydrate displays characteristic peaks at the following 2θ (two-theta) positions 6.89°±0.5°, 10.84°±0.5°, 11.48°±0.5°, 13.73°±0.5°, 15.85°±0.5°, 17.61°±0.5°, 18.51°±0.5°, 19.98°±0.5°, 21.42°±0.5°, 22.99°±0.5°, 23.27°±0.5°, 24.11°±0.5°, 24.76°±0.5°, 27.37°±0.5°, 27.99°±0.5°, 31.43°±0.5°, 34.20°±0.5°.

Experimental Example 1

Stability of 3,4-dihydro-2H-pyrido[4,3-b][1,4]oxazine HBr salt (dihydrobromide, 2HBr)

Stability comparison experiments were performed for 3,4-dihydro-2H-pyrido[4,3-b][1,4]oxazine HBr salt (2HBr) according to the present invention prepared in Example 1 and different salt forms prepared by the same process. 3,4-Dihydro-2H-pyrido[4,3-b][1,4]oxazine phosphate was obtained in gel form rather than in solid form. 3,4-dihydro-2H-pyrido[4,3-b][1,4]oxazine hydrochloride also was unstable in a semi-solid form. Only 3,4-dihydro-2H-pyrido[4,3-b][1,4]oxazine HBr salt (2HBr) and 3,4-dihydro-2H-pyrido[4,3-b][1,4]oxazine sulfate were obtained in solid form.

As shown in Table 1 below, in the case of the sulfate form, not only the purity of the obtained material became lower than that of the free base form of 3,4-dihydro-2H-pyrido[4,3-b][1,4]oxazine, but also a phenomenon occurred in the stability test wherein the solid melted again to a liquid. In contrast, in the case of the HBr salt, not only was the purity improved over that of the free base form, but also the stability test for 4 weeks showed no significant change compared to the initial purity.

TABLE 1

Stability comparison experiment results

| No. | Type | Initial purity | Condition | 1 week | 2 weeks | 4 weeks | Note |
|---|---|---|---|---|---|---|---|
| 1 | Free base | 99.36% | 30° C., 65% RH | 97.72% | 97.96% | 98.18% | >97.5% |
|   |   |   | 40° C., 75% RH | 97.74% | 97.91% | 98.10% |   |
| 2 | Bromate | 99.79% | 30° C., 65% RH | 99.89% | 99.61% | 99.58% | stable |
|   |   |   | 40° C., 75% RH | 99.89% | 99.61% | 99.56% |   |
| 3 | Sulfate | 98.88% | 30° C., 65% RH | 99.05% | 99.85% | melted | unstable |
|   |   |   | 40° C., 75% RH | melted | melted | melted |   |

In addition, for the HBr salt form, the sulfate form and the free base form, NMR was measured, and thermogravimetric (TG) analysis and differential thermal analysis (DTA) were carried out.

The NMR data of the HBr salt (2HBr) are shown in FIG. 1, and thermogravimetric (TG)/differential thermal analysis (DTA) results of the same are shown in FIG. 2.

Figure 5:
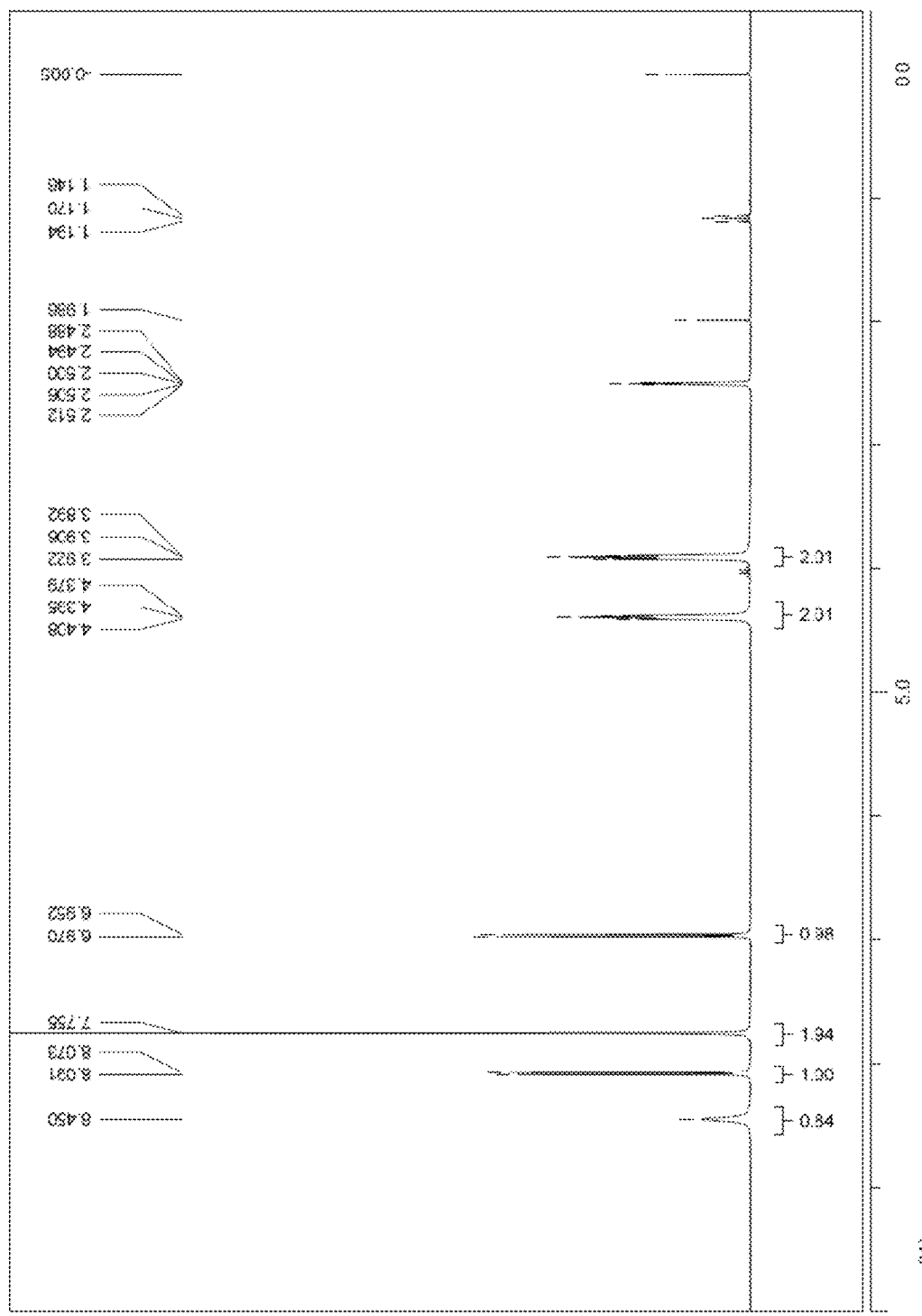
FIG. 5 shows the NMR data of 3,4-dihydro-2H-pyrido[4,3-b][1,4]oxazine sulfate.
Figure 6:
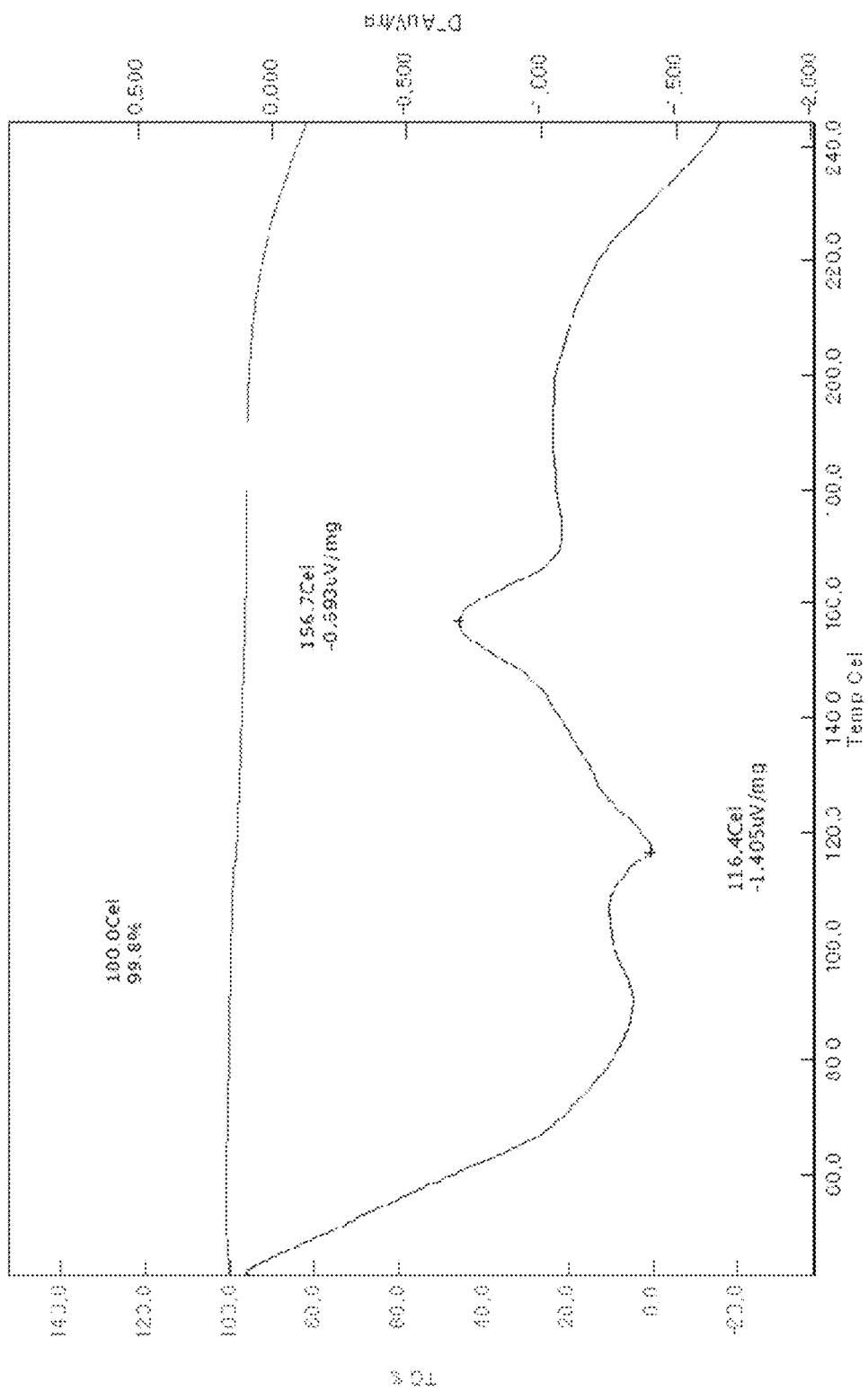
FIG. 6 shows the TG/DTA results of 3,4-dihydro-2H-pyrido[4,3-b][1,4]oxazine sulfate.

In addition, the NMR data of the sulfate are shown in FIG. 5, and TG/DTA results of the same are shown in FIG. 6.

Figure 7:
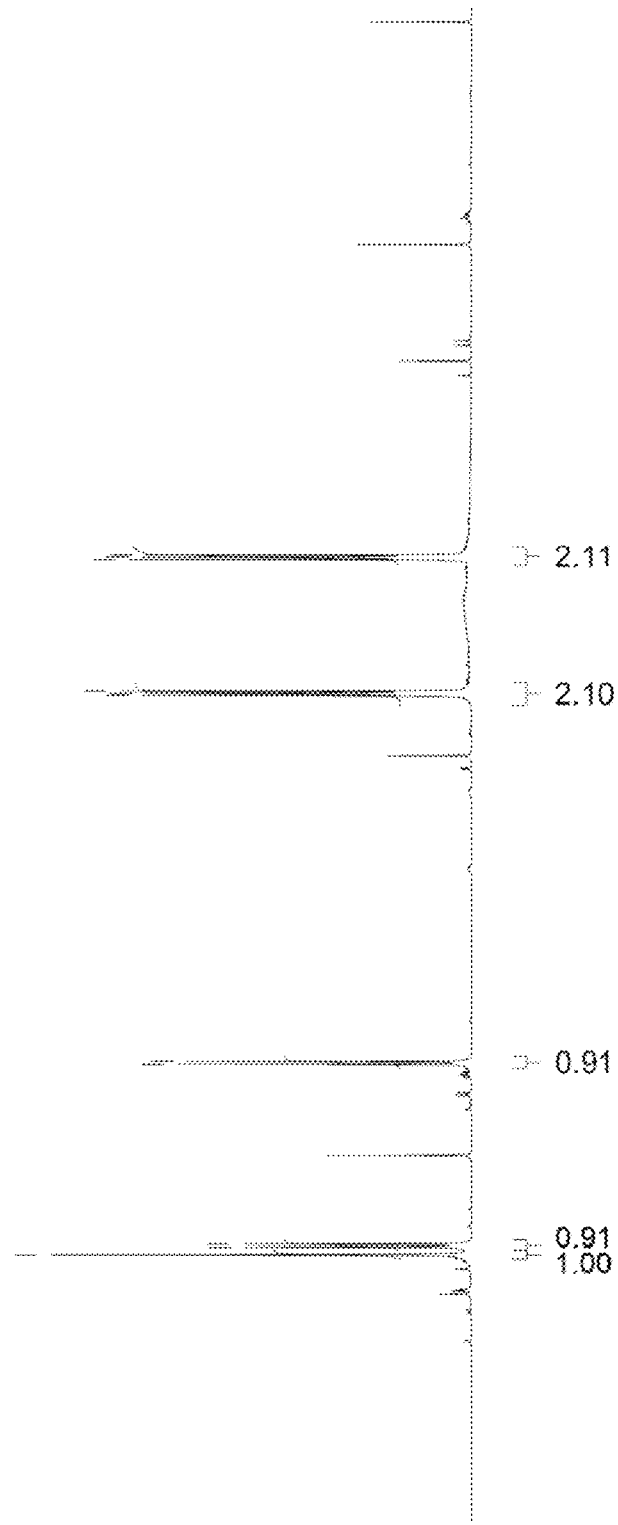
FIG. 7 shows the NMR data of 3,4-dihydro-2H-pyrido[4,3-b][1,4]oxazine free base form.
Figure 8:
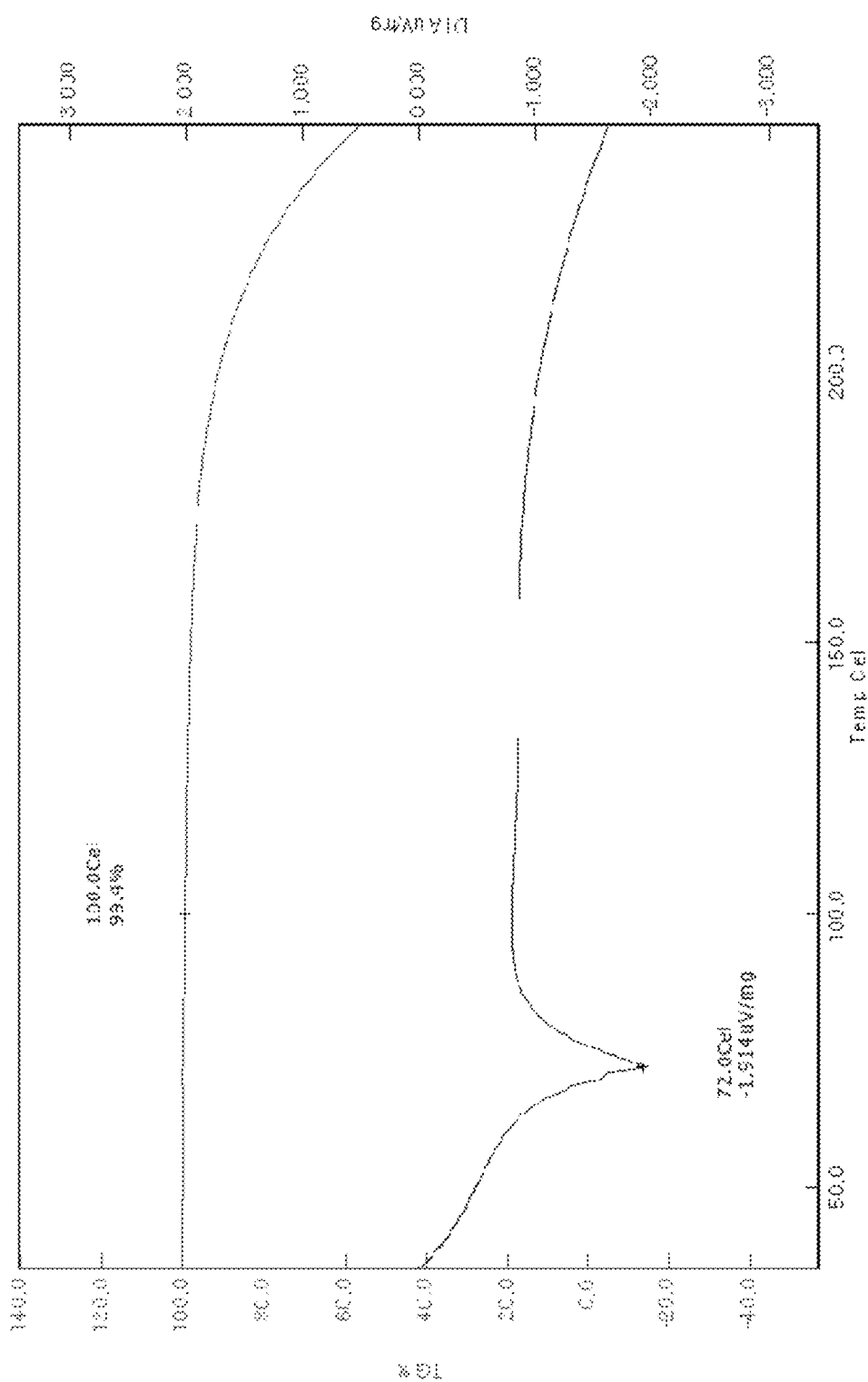
FIG. 8 shows the TG/DTA results of 3,4-dihydro-2H-pyrido[4,3-b][1,4]oxazine free base form.

In addition, the NMR data of the free base are shown in FIG. 7, and TG/DTA results of the same are shown in FIG. 8.

Experimental Example 2

Figure 9:
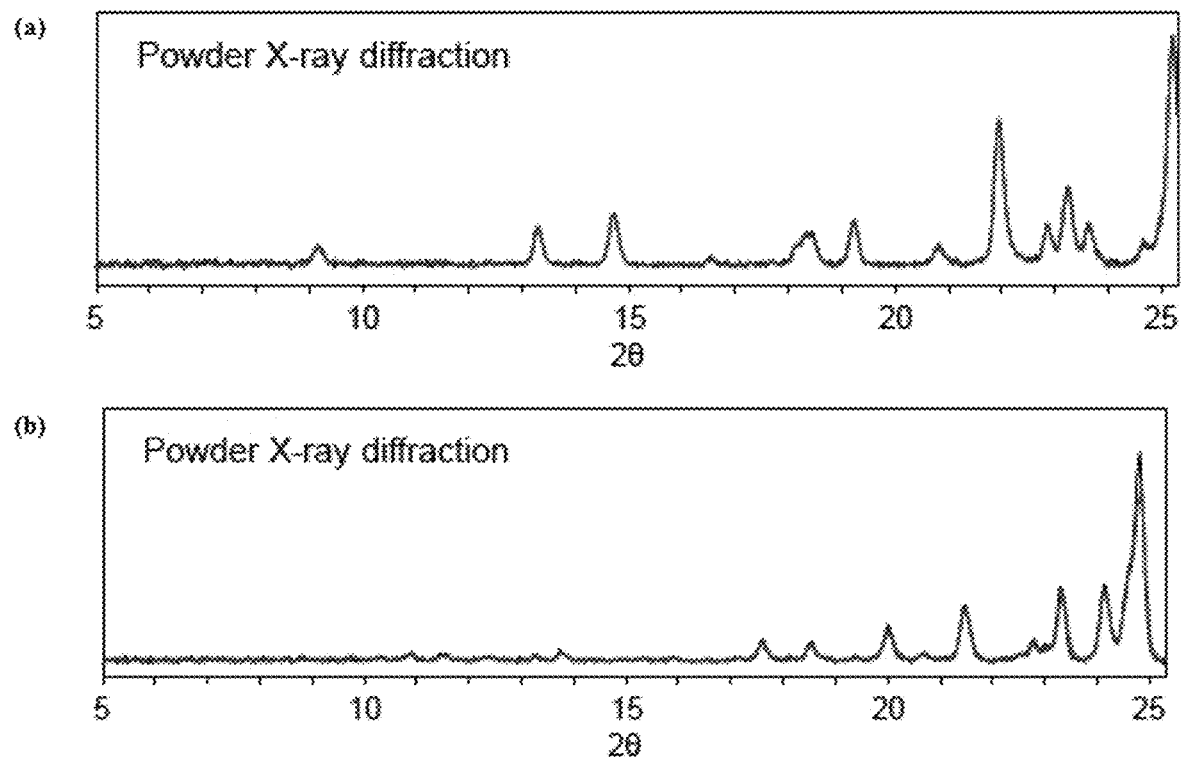
FIG. 9 shows the powder X-ray diffraction (XRD) analysis results of hydrochloride non-solvate of the compound of Formula I (a) and hydrochloride 1.5 hydrate of the compound of Formula I according to the present invention (b).
Figure 10:
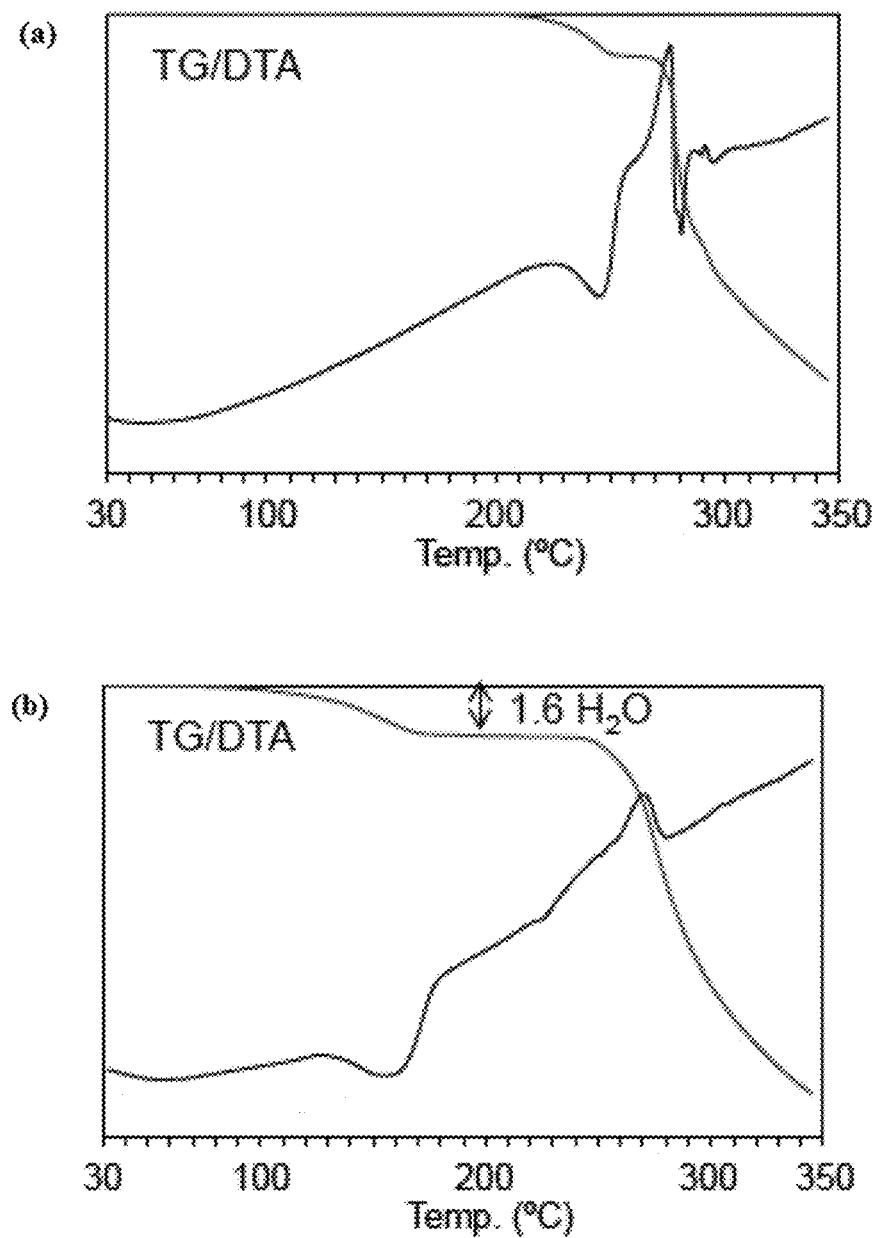
FIG. 10 shows the TG/DTA results of hydrochloride non-solvate of the compound of Formula I (a) and hydrochloride 1.5 hydrate of the compound of Formula I according to the present invention (b).
Figure 11:
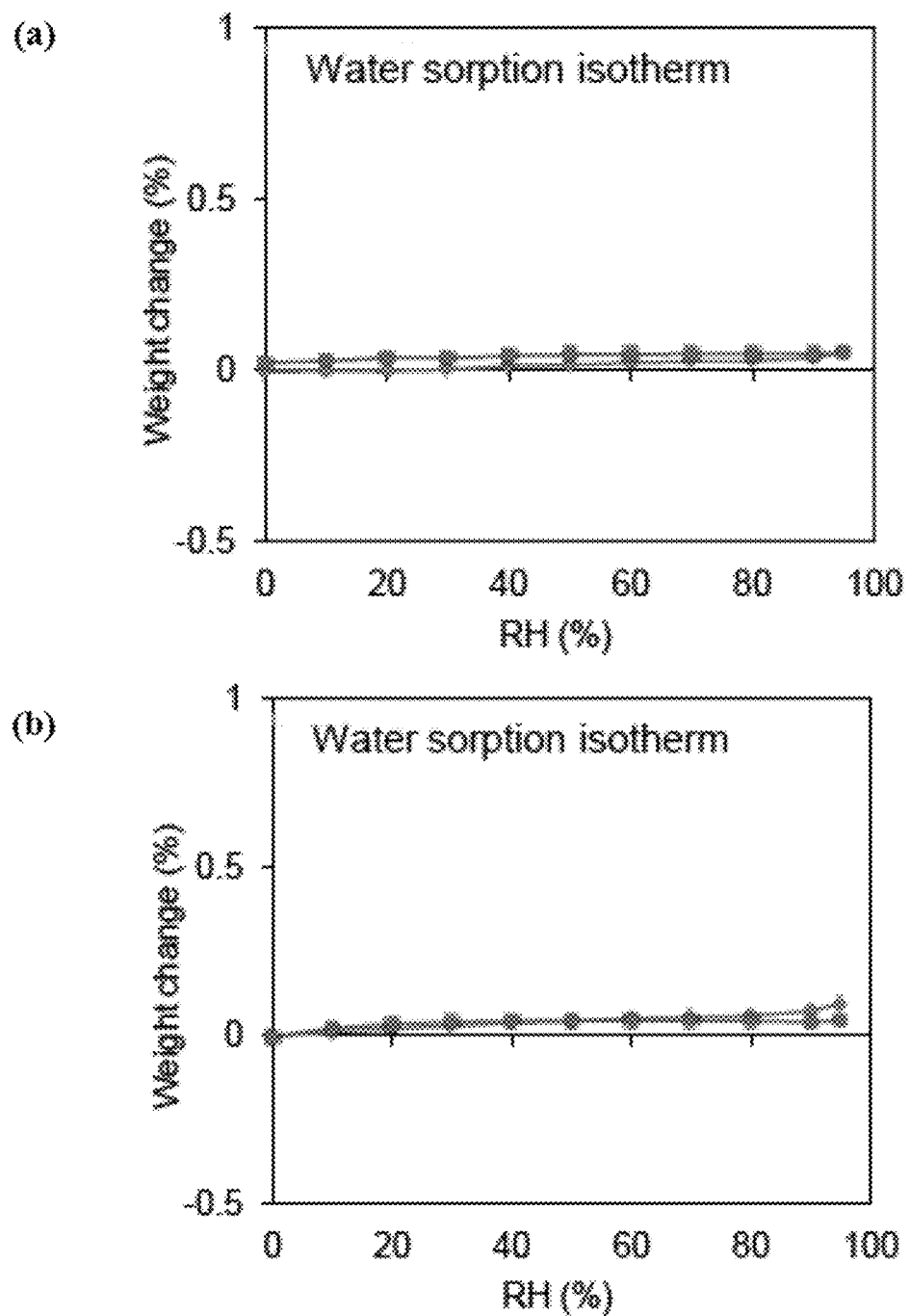
FIG. 11 shows the water sorption isotherm of hydrochloride non-solvate of the compound of Formula I (a) and hydrochloride 1.5 hydrate of the compound of Formula I according to the present invention (b).

Stability of (3,5-dibromo-4-hydroxyphenyl)(2,3-dihydro-4H-pyrido[4,3-b][1,4]oxazin-4-yl)-methanone hydrochloride 1.5 hydrate For (3,5-dibromo-4-hydroxyphenyl)(2,3-dihydro-4H-pyrido[4,3-b][1,4]oxazin-4-yl)-methanone hydrochloride 1.5 hydrate according to the present invention prepared in Example 3 and hydrochloride non-solvate of the same compound, the powder X-ray diffraction (XRD) analysis, TG/DTA and water sorption isotherm were measured, and the results are shown in FIGS. 9 to 11.

Specifically, the powder X-ray diffraction (XRD) analysis results of the non-solvate (a) and the 1.5 hydrate (b) are shown in FIG. 9.

The TG/DTA results of the non-solvate (a) and the 1.5 hydrate (b) are shown in FIG. 10.

The water sorption isotherms of the non-solvate (a) and the 1.5 hydrate (b) are shown in FIG. 11.

In addition, the physical stability to processing factors in the preparation of the above 1.5 hydrate and the non-solvate were compared, and the results are shown in Table 2 below.

TABLE 2

Comparison of physical stability to processing factors

| Test condition | Evaluation after processing | HCl non-solvate form | HCl 1.5 hydrate form |
|---|---|---|---|
| Grinding* | Crystallinity change**** | Δ8% (97→89%) | Δ3% (94→91%) |
| Granulating with water** | Solid form | Mixture with HCl 1.5 hydrate form | Unchanged |
| Granulating with 1:1 of water and ethanol** | Solid form | Mixture with HCl 1.5 hydrate form | Unchanged |
| Tableting*** | Crystallinity change**** | Δ8% (97→90%) | Δ5% (94→89%) |

*Samples were ground for about 2 min using a mortar.
**After adding 30% v/w solvent, samples were granulated for about 2 min using mortar. After storing granulated samples in closed vials for about 1 h, samples were dried at 50° C. for about 3 hr.
***Samples were pressed at 2 tons of pressure for 5 sec using 7 mm plat-faced punches.
****Crystallinities were evaluated using a powder X-ray diffractometer.

As shown in Table 2 above, as a result of comparing crystallinity changes in grinding and tableting, the 1.5 hydrate was much more stable than the non-solvate. In addition, as a result of comparing solid forms in granulating, it was observed that the non-solvate was partially transformed into the 1.5 hydrate, whereas the 1.5 hydrate showed no change. Therefore, it was understood that the 1.5 hydrate shows better physical stability than the non-solvate.

Experimental Example 3

Figure 12:
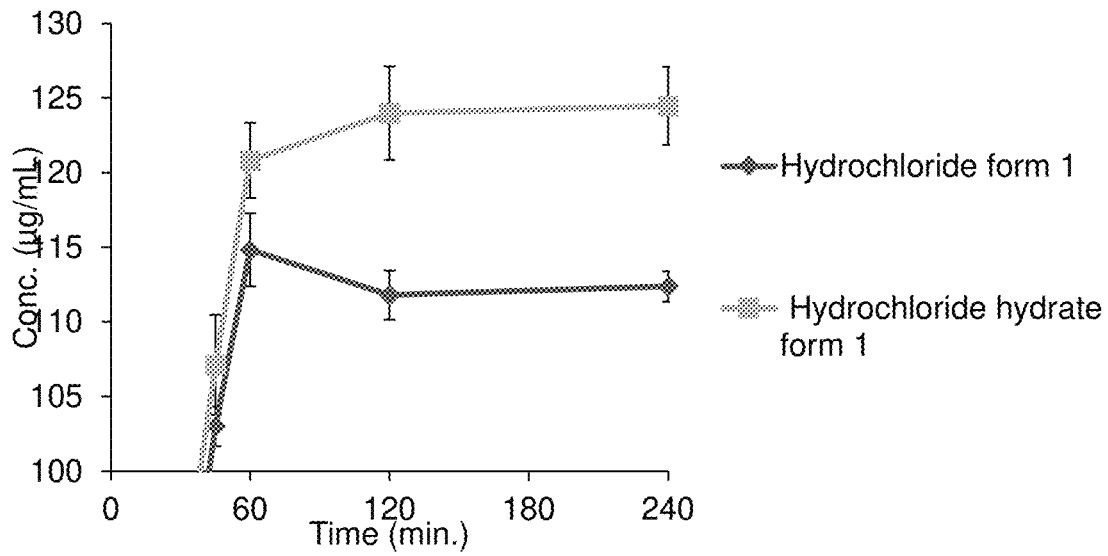
FIG. 12 shows the solubility of hydrochloride 1.5 hydrate of the compound of Formula I according to the present invention in comparison with that of hydrochloride non-solvate of the same compound.

Solubility of (3,5-dibromo-4-hydroxyphenyl)(2,3-dihydro-4H-pyrido[4,3-b][1,4]oxazin-4-yl)-methanone hydrochloride 1.5 hydrate Solubility was compared between (3,5-dibromo-4-hydroxyphenyl)(2,3-dihydro-4H-pyrido[4,3-b][1,4]oxazin-4-yl)-methanone hydrochloride 1.5 hydrate according to the present invention prepared in Example 3 and hydrochloride non-solvate of the same compound. The solubility test was carried out using 50 mL of FeSSIF (pH 5.0) as a medium and setting the paddle speed at 50 rpm under the operation condition at 37° C. The solubility was measured using a physical mixture of 10 mg of the compound and 100 mg of lactose as a sample. The results are shown in FIG. 12. At 240 minutes, the solubility of the hydrochloride 1.5 hydrate was about 125 µg/mL, whereas the solubility of the non-solvate was decreased to about 112.5 µg/mL.

Experimental Example 4

Comparison of the Effects per Dose of (3,5-dibromo-4-hydroxyphenyl)(2,3-dihydro-4H-pyrido[4,3-b][1,4]oxazin-4-yl)-methanone For a total of 60 gout patients, (3,5-dibromo-4-hydroxyphenyl)(2,3-dihydro-4H-pyrido[4,3-b][1,4]oxazin-4-yl)- methanone hydrochloride 1.5 hydrate according to the present invention prepared in Example 3 was administered. The compound was orally administered at doses of 0.25 mg (N=12), 0.5 mg (N=12), 1 mg (N=12) and 2 mg (N=12) based on the active ingredient (3,5-dibromo-4-hydroxyphenyl)(2,3-dihydro-4H-pyrido[4,3-b][1,4]oxazin-4-yl)-methanone (Formula I), and placebo (N=12), for 14 days. The efficacy and safety of the compound on the serum uric acid (UA) level was evaluated in comparison with the placebo.

Serum uric acid levels were measured on the 15th day after administration, and the percentages of patients whose serum uric acid level fell below <6.0 mg/dL and below <5.0 mg/dL were determined and shown in FIG. 13. As shown in FIG. 13, in the case of administration of the compound at doses of 0.25 mg, 0.5 mg and 1 mg, no patient showed the serum uric acid level below <5.0 mg/dL, and only in the case of 2 mg dose the percentage was merely about 8%. From the above results, it could be understood that a dose less than 2 mg is not effective in the treatment of diseases such as hyperuricemia and gout.

In addition, for a total of 68 gout patients, (3,5-dibromo-4-hydroxyphenyl)(2,3-dihydro-4H-pyrido[4,3-b][1,4]oxazin-4-yl)-methanone hydrochloride 1.5 hydrate according to the present invention was administered. The compound was orally administered at doses of 3 mg (N=13), 5 mg (N=14), 7 mg (N=15) and 10 mg (N=15) based on the active ingredient (3,5-dibromo-4-hydroxyphenyl)(2,3-dihydro-4H-pyrido[4,3-b][1,4]oxazin-4-yl)-methanone (Formula I), and placebo (N=11), for 14 days. The efficacy and safety of the compound on the serum uric acid level was evaluated in comparison with the placebo.

Serum uric acid levels were measured on the 15th day after administration, and the percentages of patients whose serum uric acid level fell below <6.0 mg/dL and below <5.0 mg/dL were determined and shown in FIG. 14. As shown in FIG. 14, in the case of administration of the compound at doses 3 mg, 5 mg, 7 mg and 10 mg, the percentages of patients whose serum uric acid level fell below <5.0 mg/dL were approximately 23%, 64%, 80% and 73%, respectively, in other words, in the range of about 23% to 80%. Patients whose serum uric acid level fell below <6.0 mg/dL also appeared in all experimental doses.

From the above experimental results, it could be understood that a significant effect occurs at a dose greater than 2 mg which is the lower limit of the dose range of the dosage regimen according to the present invention.

Experimental Example 5

Review of the Side Effects per Dose of (3,5-dibromo-4-hydroxyphenyl)(2,3-dihydro-4H-pyrido[4,3-b][1,4]oxazin-4-yl)-methanone For a total of 76 gout patients, (3,5-dibromo-4-hydroxyphenyl)(2,3-dihydro-4H-pyrido[4,3-b][1,4]oxazin-4-yl)-methanone hydrochloride 1.5 hydrate according to the present invention prepared in Example 3 was administered. The compound was orally administered at doses 3 mg (N=14), 5 mg (N=15), 7 mg (N=17) and 10 mg (N=17) based on the active ingredient (3,5-dibromo-4-hydroxyphenyl)(2,3-dihydro-4H-pyrido[4,3-b][1,4]oxazin-4-yl)-methanone (Formula I), and placebo (N=13), for 14 days, and the adverse drug reaction was investigated. As a result, as shown in Table 3 below, the above dosage regimen showed no or very low incidence of adverse events such as arthralgia and joint swelling.

TABLE 3

| | Adverse drug reaction | | | | |
|---|---|---|---|---|---|
| Type | Placebo (N = 13) | 3 mg (N = 14) | 5 mg (N = 15) | 7 mg (N = 17) | 10 mg (N = 17) |
| arthralgia | 0 | 0 | 0 | 0 | 2 persons (11.76%) [3 cases] |
| joint swelling | 0 | 0 | 0 | 0 | 1 person (5.88%) [1 case] |

Furthermore, urinary creatinine levels were also measured in the same patients. The number of cases in which creatinine is increased by more than 0.3 mg/dL or more than 1.5 times compared to baseline is shown in Table 4 below.

TABLE 4

The number of cases in which creatinine is increased by more than 0.3 mg/dL or more than 1.5 times compared to baseline

| Dose | Number of cases |
|---|---|
| Placebo | 1 |
| 5 mg | 1 |
| 10 mg | 3 |

As shown in Table 4 above, only one case was observed commonly in the placebo group and in the 5 mg dose group, whereas 3 cases were observed in the 10 mg dose group which is the maximum dose. From the above results, it could be inferred that the risk of increasing urinary creatinine concentration is higher when a dose exceeds the maximum dose of 10 mg.

What is claimed is:

1. A compound of the following Formula III:

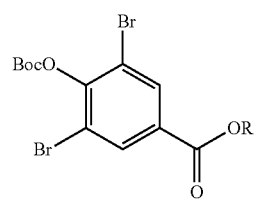

wherein R is hydrogen or Boc.

2. A compound of the following Formula IV:

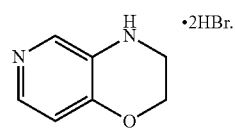

* * * * *